(12) United States Patent
Glaberson et al.

(10) Patent No.: US 10,295,499 B2
(45) Date of Patent: May 21, 2019

(54) FERROUS METALS MEASURING MAGNETOMETER SYSTEM AND METHOD

(71) Applicant: Spectro Scientific, Inc., Chelmsford, MA (US)

(72) Inventors: John Glaberson, Sandy Hook, CT (US); Patrick F. Henning, Concord, MA (US)

(73) Assignee: Spectro Scientific, Inc., Chelmsford, MA (US)

( * ) Notice: Subject to any disclaimer, the term of this patent is extended or adjusted under 35 U.S.C. 154(b) by 0 days.

(21) Appl. No.: 15/434,293

(22) Filed: Feb. 16, 2017

(65) Prior Publication Data
US 2018/0231497 A1     Aug. 16, 2018

(51) Int. Cl.
*G01N 27/02*     (2006.01)
*G01N 27/72*     (2006.01)
*G01N 33/28*     (2006.01)

(52) U.S. Cl.
CPC ........... *G01N 27/72* (2013.01); *G01N 27/023* (2013.01); *G01N 33/28* (2013.01)

(58) Field of Classification Search
None
See application file for complete search history.

(56) References Cited

U.S. PATENT DOCUMENTS

| | | |
|---|---|---|
| 4,563,644 A | 1/1986 | Lenander et al. |
| 4,613,815 A | 9/1986 | Christel, Jr. |
| 4,686,469 A * | 8/1987 | Lewis ................. G01N 15/0656 324/204 |
| 4,926,120 A | 5/1990 | Veronesi et al. |
| 5,001,424 A | 3/1991 | Kellett et al. |
| 5,041,856 A | 8/1991 | Veronesi et al. |
| 5,262,732 A | 11/1993 | Dickert et al. |
| 5,315,243 A | 5/1994 | Kempster et al. |
| 5,404,100 A | 4/1995 | Burnett et al. |
| 5,433,196 A * | 7/1995 | Fiat ..................... G01R 33/5601 600/410 |
| 5,444,367 A | 8/1995 | Kempster et al. |
| 5,811,664 A | 9/1998 | Whittington et al. |
| 6,051,970 A | 4/2000 | Hutchings |
| 6,346,813 B1 * | 2/2002 | Kleinberg ............ G01N 24/081 324/303 |
| 6,891,369 B2 * | 5/2005 | Hurlimann ........... G01N 24/081 324/303 |
| 7,737,683 B2 | 6/2010 | Graze et al. |

(Continued)

FOREIGN PATENT DOCUMENTS

| | | |
|---|---|---|
| WO | 2004104561 A1 | 12/2004 |
| WO | 2007088015 A1 | 8/2007 |

*Primary Examiner* — Paresh H Patel
(74) *Attorney, Agent, or Firm* — Iandiorio Teska & Coleman, LLP

(57) ABSTRACT

A method of and system for determining the total magnetic content of a fluid sample introduced within at least one coil. A sample withdrawal event time is determined and, at the sample withdrawal event time, the response of the at least one coil is analyzed in two zones, a first zone before the fluid sample withdrawal event time and a second zone after the fluid sample withdrawal event time. The total magnetic content of the fluid is calculated based on the difference in the response of the at least one coil in the first and second zones at the fluid sample withdrawal event time.

13 Claims, 15 Drawing Sheets

(56) References Cited

U.S. PATENT DOCUMENTS

| | | |
|---|---|---|
| 7,784,332 B2 | 8/2010 | Cho et al. |
| 8,115,478 B2 | 2/2012 | Fujii et al. |
| 8,354,836 B2 | 1/2013 | Becker et al. |
| 8,522,604 B2 | 9/2013 | Zhe et al. |
| 9,274,041 B2 | 3/2016 | Henning et al. |
| 2003/0178994 A1* | 9/2003 | Hurlimann ........... G01N 24/081 324/303 |
| 2006/0152213 A1 | 7/2006 | Thompson et al. |
| 2016/0104604 A1* | 4/2016 | Kim ................... H01J 37/32119 156/345.27 |
| 2017/0269036 A1* | 9/2017 | Foord ................. G01N 27/023 |

* cited by examiner

FERROUS METALS MEASURING MAGNETOMETER SYSTEM AND METHOD

FIELD OF THE INVENTION

This invention relates to fluid sample ferrous metals measurement devices and methods.

BACKGROUND OF THE INVENTION

The total ferrous content (in ppm) of a fluid sample can be measured by the response of a coil about the fluid sample. See for example U.S. Pat. Nos. 4,563,644, 4,613,815, 4,926,120, 5,001,424, 5,041,856, 5,315,243, 5,404,100, 5,444,367, 5,811,664, 6,051,970, 7,737,683, 7,784,332, 8,115,478, 8,354,836, 8,522,604, US20060152213, WO2004104561, and WO2007088015 all incorporated herein by reference. The ferrous particles have a magnetic permeability and the permeability of the particles increases the inductance of the coil.

A typical way to measure inductance is to supply a known AC current to the coil and measure the voltage across the coil. Using this method, it is necessary to measure a small change in a large voltage. The measuring circuit should then be extremely stable and have a wide dynamic range. For example, if a resolution of 1 ppm ferrous content is desired, the measuring circuit would have to have a dynamic range of about 14,000,000:1.

Additionally, the coil itself is not very stable with temperature. This is caused by the thermal expansion of the wire and bobbin and the fact that the permeability of the ferrite shield has a large temperature coefficient. Together, these factors probably produce an inductance temperature coefficient of about 500 PPM/° C. Thus a 1° C. change in coil temperature would change the inductance about 70 times as much as the sample. In addition, the temperature coefficient of resistance is about 3900 PPM/° C., which would change the overall impedance about 5500 times as much as the sample.

One solution to this problem is to put two identical coils in series and to use them as a voltage divider. One coil is the active coil and receives the sample while the other identical coil is a dummy coil that never receives a sample. The coil pair is driven with a sinusoidal voltage of about 8V p-p at 22 kHz. The power dissipated by the coil drive can increase the coil temperature by 10-15° C. Both coils increase in temperature by about the same amount, so balance is maintained over temperature.

With the voltage divider, there is still the problem of measuring a small change in a large voltage. This problem is solved by providing each coil with a secondary winding and connecting the secondaries in anti-series. Such a difference coil arrangement allows the nominal output voltage to be reduced to zero. It also allows the output to be increased by using a turns ratio greater than one.

With the introduction of the sample, the voltage at the junction of the primary voltage divider changes from 4 Vp-p to 4.000014 Vp-p for a 100 ppm sample. At the output of the secondaries, the voltage changes from 0 to 68 microvolts.

See also U.S. Pat. No. 9,274,041 incorporated herein by this reference.

BRIEF SUMMARY OF THE INVENTION

Still, if the fluid sample is at a different temperature than the coil and/or if the ambient temperature changes the temperature of the coil, the response of the coil will include distortions that can affect the determination of the total magnetic content of the fluid sample.

In a flow-through system such as disclosed in U.S. Pat. No. 9,274,041 where the fluid sample is pumped through one or more magnetometers, the temperature of the system is fairly stable. Still, solvents must be used to flush the system between the analysis of different samples and the cost of such a flow-through system can be high.

In other systems such as disclosed in U.S. Pat. No. 6,051,970 a portion of fluid is gathered from a flow line and placed into a closed container. The ferrous content of the fluid is then determined by placing the container in a measuring device. In general such systems can be highly sensitive to ferrous content but due to such distortions of the coil response can provide unstable readings, which may limit the effectiveness of such an apparatus. The present invention eliminates this obstacle by directly measuring the response of the coil due to temperature changes of the coil and utilizes this information to provide a distortion-free calculation of the total magnetic content of the fluid. In this way, a closed container such as a capped syringe can be used to conveniently introduce the sample to the coil resulting in a solvent free, lower cost, yet highly accurate and stable system.

Featured is a method of determining the total magnetic content of a fluid sample introduced within at least one coil. The method comprises determining a sample withdrawal event time and, at the sample withdrawal event time, analyzing the response of the at least one coil in two zones, a first zone before the fluid sample withdrawal event time and a second zone after the fluid sample withdrawal event time. The total magnetic content of the fluid is calculated based on the difference in the response of the at least one coil in the first and second zones at the fluid sample withdrawal event time. One preferred method may further include determining a sample insertion event time and, at the sample insertion event time, analyzing the response of the at least one coil in two zones, a third zone before the fluid sample insertion event and a fourth zone after the fluid sample insertion event time. The total magnetic content of the fluid sample is then determined based on weighted values of a) the difference in the response of the at least one coil in the first and second zones at the fluid sample withdrawal event time and b) the difference in the response of the at least one coil in the third and fourth zones at the fluid sample insertion event time.

Analyzing the response of the at least one coil may include calculating curve fits to the coil response in the first and second zones. One type of curve fit that can be used is a linear regression. Other types could include quadratic regression, cubic spline, or other known methods. The following description uses linear regression as an example. Determining the fluid sample withdrawal event time may include employing one or more sensors to detect an initial fluid sample withdrawal event time and may further include adjusting the initial fluid sample withdrawal event time based on the response of the coil between the linear regressions. Analyzing the response of the at least one coil may include calculating linear regressions of the coil response in the third and fourth zones. Determining the fluid sample insertion event time may include employing one or more sensors to detect an initial fluid sample insertion event time. Determining the fluid sample insertion event time may further include adjusting the initial fluid sample insertion event time based on the response of the coil between the linear regressions. Analyzing the response of the coil(s) may include analyzing a real and/or imaginary components of the coil response.

Also featured is a ferrous metals measuring magnetometer system comprising a chamber for receiving a container with a fluid sample therein and at least one coil about the chamber which changes in inductance due to ferrous metals in the fluid sample and due to temperature changes of the coil. At least a first sensor subsystem is associated with the chamber for detecting a container withdrawal event. A controller subsystem is responsive to a response of the coil and the first sensor subsystem and programmed to: determine the response of the coil due to ferrous metals present in the fluid sample at the withdrawal event, determine the response of the coil due to temperature changes of the coil at the withdrawal event, and calculate the total magnetic content of the fluid based on the determination of the response of the coil due to ferrous metals present in the fluid sample at the withdrawal event and the determination of the response of the coil due to temperature changes of the coil at the withdrawal event.

The controller subsystem may further be configured to determine a withdrawal event time and to determine the response of the coil in a first zone before the withdrawal event time and in a second zone after the withdrawal event time and to perform linear regressions of the coil response in the first and second zones. The controller subsystem may be configured to calculate the total magnetic content of the fluid sample from the difference in the linear regression values of the coil response in both zones at the withdrawal event time. The controller subsystem may be further configured to adjust the withdrawal event time based on the response of the coil between the linear regressions.

The system may further include a second sensor subsystem for determining a container insertion-event time and then the controller subsystem is further programmed to determine the response of the coil in a third zone before the insertion event time and in a fourth zone after the insertion event time. The controller subsystem may be further configured to perform linear regressions of the coil response in the third and fourth zones. The controller subsystem may be further configured to calculate the total magnetic content of the fluid based on the difference of the linear regressions of the coil response in the first and second zones at the withdrawal event time and the difference of the linear regressions of the coil response in the third and fourth zones at the insertion event time. Preferably, the controller subsystem is configured to calculate the total magnetic content based on weighted values of a) the difference of the linear regressions of the coil response in the first and second zones at the withdrawal event time and b) the difference of the linear regressions of the coil response in the third and fourth zones at the insertion event time. The controller subsystem may be further configured to adjust the insertion event time based on the response of the coil between the linear regressions.

There may be one or more additional coils about the chamber connected to the controller subsystem via an electronic section. Preferably, the electronics section is configured to resolve imaginary and real components of the coil response.

Also featured is a method for determining the total magnetic content of a fluid sample, the method comprising: analyzing the response of at least one coil at a fluid sample insertion event into the coil; analyzing the response of the at least one coil at a fluid sample withdrawal event from the coil; and calculating a total magnetic content of the fluid sample based on the response of the coil at the sample insertion event and the sample withdrawal event. Preferably, the total magnetic content is calculated based on weighted values of the response of the at least one coil at the fluid sample insertion event and the response of the at least one coil at the fluid sample withdrawal event.

Also featured is a ferrous metals measuring magnetometer system comprising a chamber for receiving a container with a fluid sample therein, at least one coil about the chamber, a sensor system associated with the chamber for detecting a container insertion event into the chamber and a container withdrawal event out of the chamber, and a controller subsystem responsive to the coil response and the sensor subsystem. The controller subsystem analyzes the response of at least one coil at the fluid sample event, analyzes the response of the at least one coil at a fluid sample withdrawal event, and calculates a total magnetic content of the fluid sample based on the response of the coil at the sample insertion event and the sample withdrawal event.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Figure 1A:
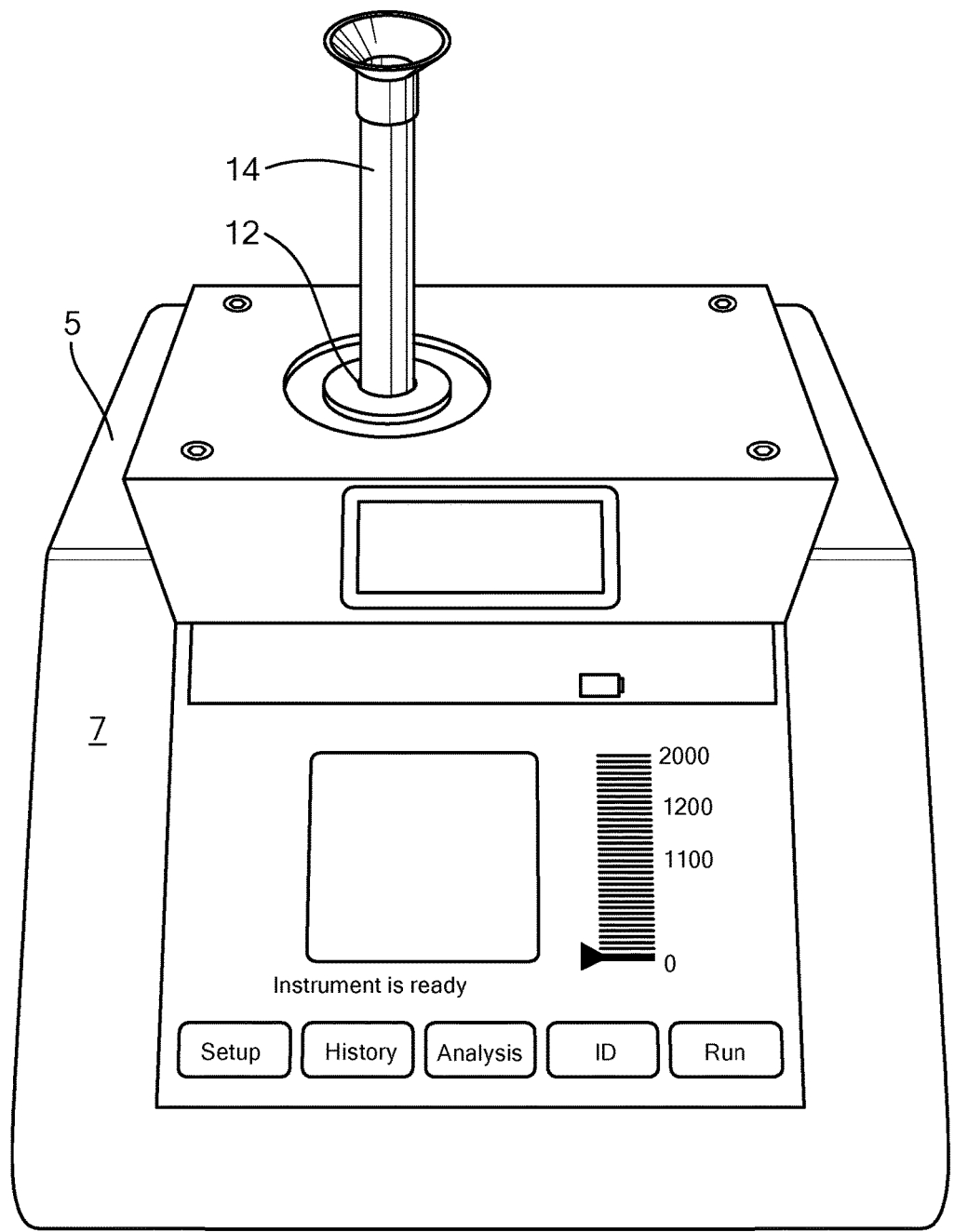
FIGS. 1A-1B are views of an example of a ferrous metals measuring magnetometer system where a vessel with the fluid under test is placed in the center hole which places the fluid in the center of the active coil bobbin.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

Figure 1B:
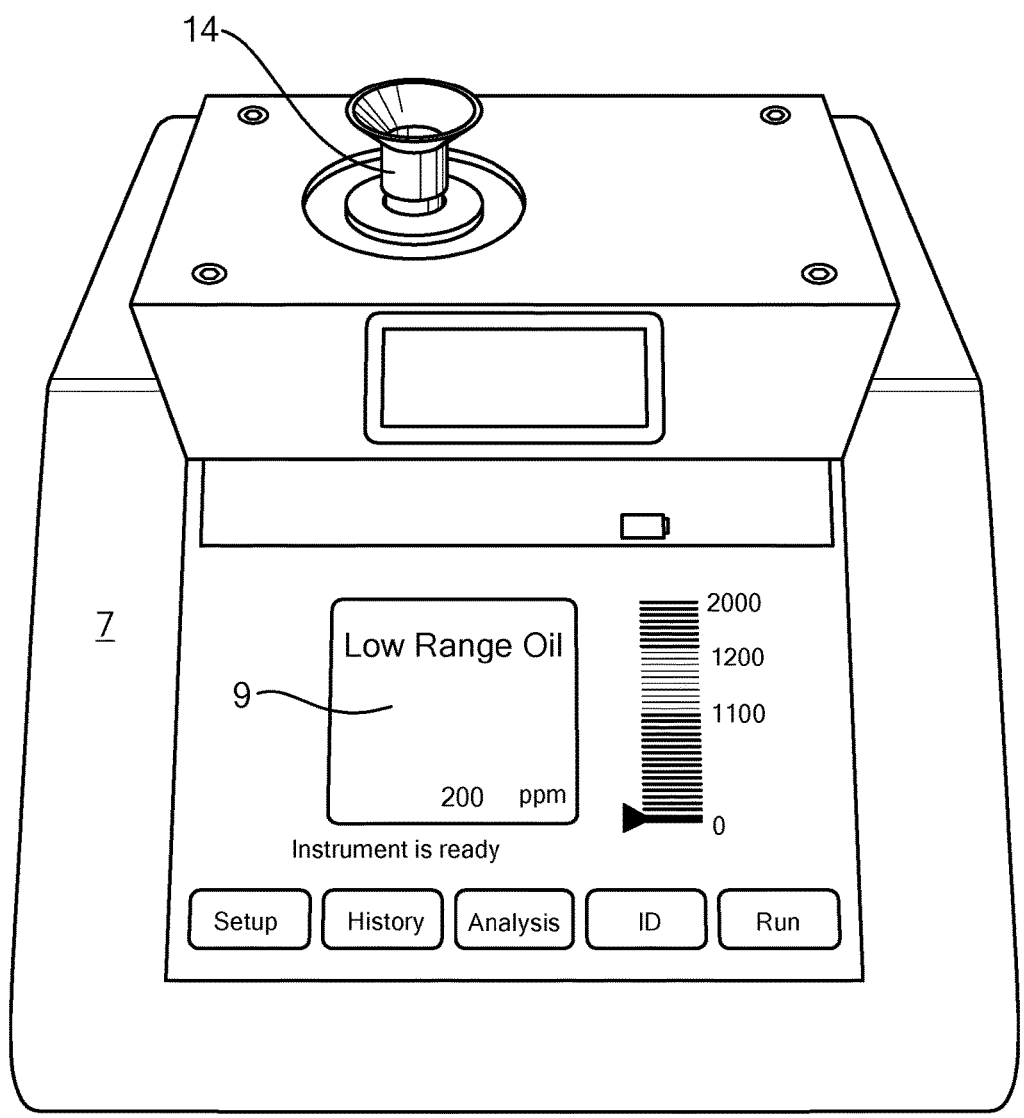

FIG. 1A shows a magnetometer system 5 where a syringe 14 with oil therein is dropped down into a chamber 12 in housing 7. FIG. 1B shows the system providing a readout on display 9 of the total magnetic content of the oil in the syringe.

Figure 1C:
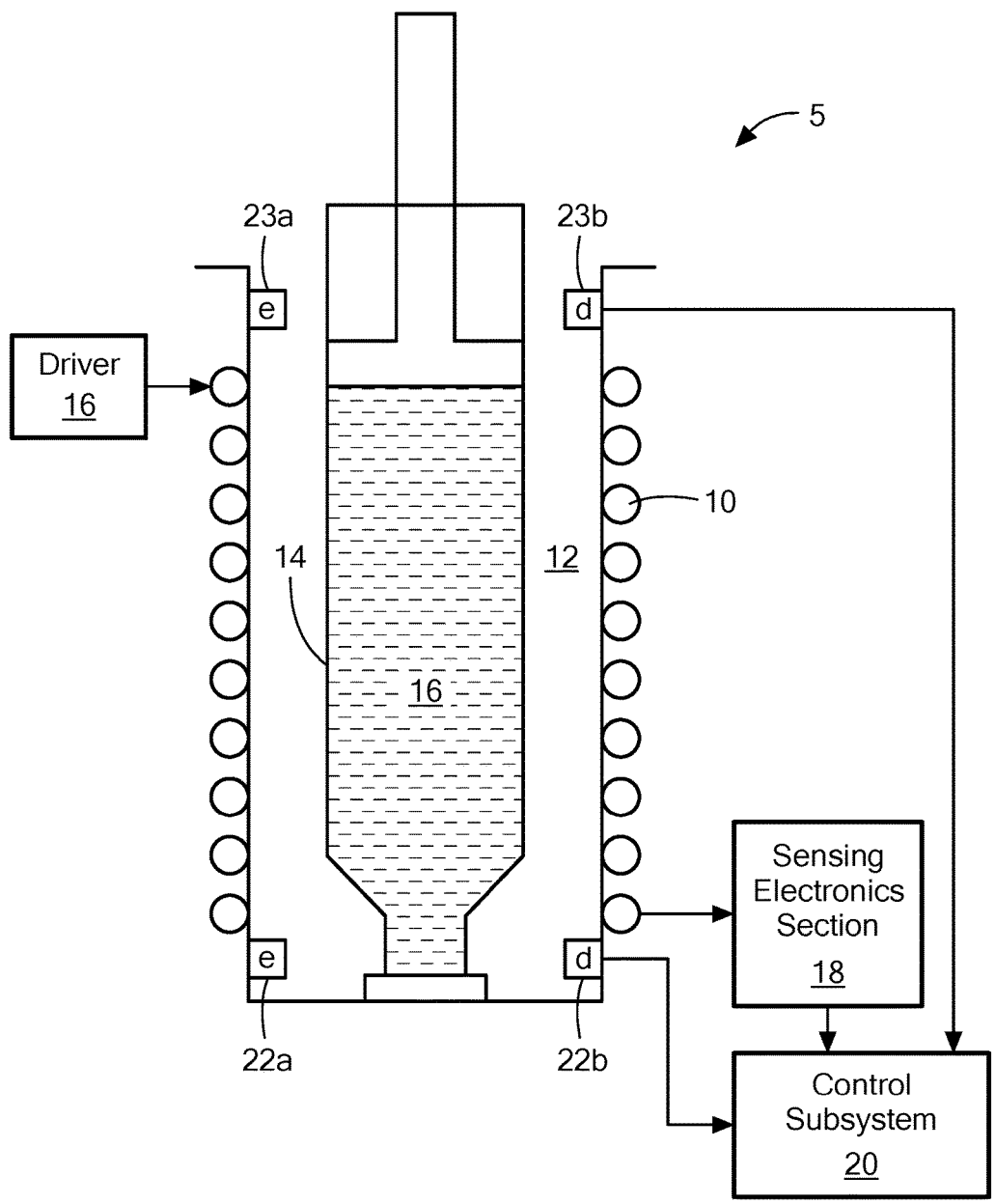
FIG. 1C is a schematic view showing the primary components associated with an example of a ferrous metals measuring magnetometer system.

FIG. 1C shows a coil 10 (e.g., made of copper) about chamber 12 configured to receive a container, e.g., a capped syringe 14 with a fluid sample 16 therein. The fluid in the syringe may have a diameter of about 0.38 inches and a length of about 3.5 inches. Typically, the syringe is used to withdraw a fluid sample from a machine such as an engine or pump. The syringe is capped and then inserted into sample chamber 12. Driver 16 supplies a known AC current to coil 10 and sensing electronic section 18 measures the voltage across the coil 10 which is processed using controller subsystem 20, for example, a microcontroller or the like running computer software as described herein. The controller system may be a standalone computer, a microcontroller, microprocessor, application specific integrated circuit, or combination of such electronic devices. The coil 10 may have an inside diameter of 0.5 inches and a length of 0.75 inches and an inductance of about 180 microhenries.

Typically, the fluid sample syringe 14 is only present in chamber 12 for about 20 seconds. During this time, the difference in the temperature of the sample and/or the syringe with respect to the temperature of the sensitive coil results in a large amount of thermal noise. In the subject invention, this thermal noise is accounted for and accuracies in the determination of the total magnetic content of the fluid sample at a level of ±5 ppm with 99% confidence can be realized. Because the system is not a flow through system, solvents need not be used and the cost of the system may be reduced.

Preferably, the system includes at least a first sensor subsystem with, in this example, LED emitter 22a and detector 22b associated with the bottom of chamber 12 used to detect when the container 16 is being withdrawn out of chamber 12. When detector 22b, for example, detects photons from emitter 22a, then does not detect photons, and then again detects photons, a withdrawal event time, $T_{out}$, step 40, FIG. 3 is set by controller subsystem's 20 response to detector 22b. $T_{out}$ shown in FIG. 2.

Figure 2:
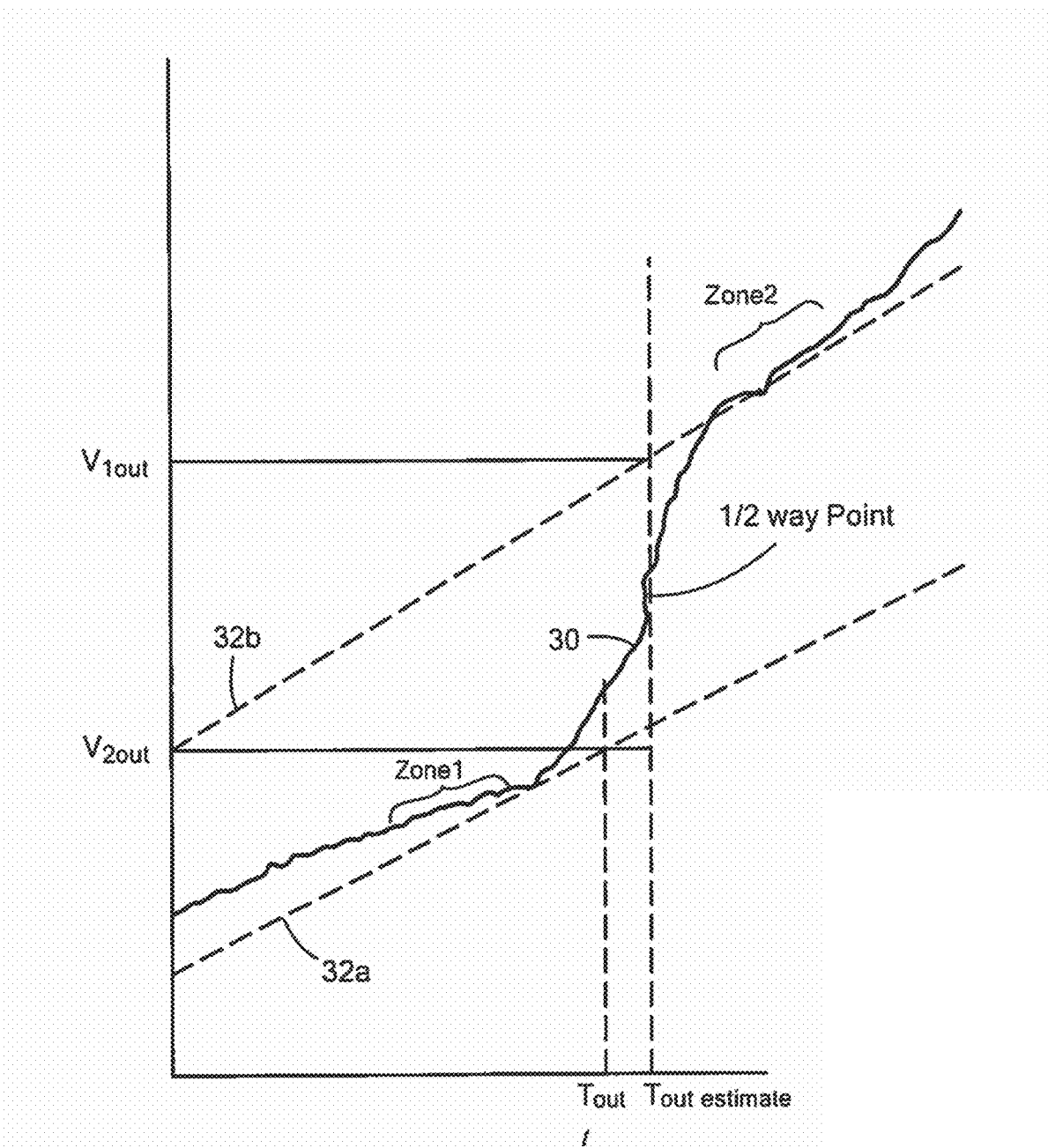
FIG. 2 is a graph showing an example of the response of the coil of FIG. 1 as the syringe container is being withdrawn from the chamber.
Figure 3:
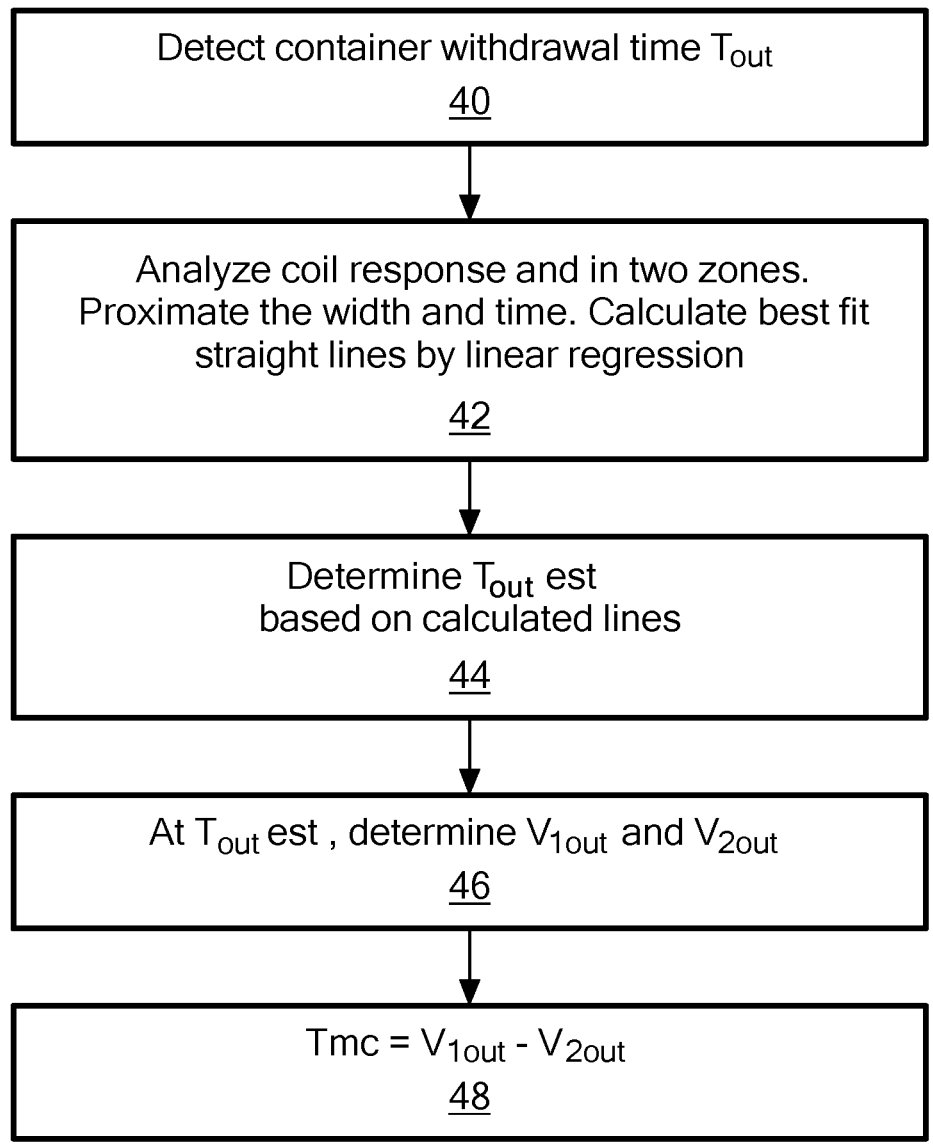
FIG. 3 is a flowchart depicting an example of the primary steps associated with the programming of the controller subsystem shown in FIG. 1 and also associated with an example of a method for more accurately determining the total magnetic content of the fluid present in the syringe of FIG. 1.

The imaginary component of the system response 30, FIG. 2, of the coil 10, FIG. 1 is then analyzed by the controller subsystem. In a window or zone of response data (zone 1) before $T_{out}$, a best fit straight line 32a ii calculated by, for example, linear regression of the data in the window. Also, using a window or zone (zone 2) of response data after $T_{out}$, another best fit straight line is calculated, for example, by linear regression of the data as shown at 32b. See step 42, FIG. 3. Such zones of response data are typically 0.25 to 0.5 seconds in duration, chosen to be short enough so that other potential pre-measurement effects do not affect the line fit and far enough away from $T_{out}$ (typically 0.1 to 0.3 seconds) so that effects due to the sudden change in signal due to the insertion event itself do not affect the line fit. The total magnetic content is then the difference between the values of each straight line 32a, 32b at time $T_{out}$.

$T_{out}$ determined solely from the LEDs may not be wholly accurate due to the different ways a sample container maybe withdrawn from the chamber. For example, in FIG. 2, the initial estimate of $T_{out}$ from the LEDs provides a smaller than actual determination of total magnetic content. Thus, $T_{out}$ may be refined by the controller subsystem as shown in FIG. 2. Here, the $T_{out}$ estimate shown in FIG. 2 is that time corresponding to a response 30 value halfway between regression lines 32a and 32b and is thus calculated by the controller subsystem at step 44, FIG. 3. At this point, $V_{1out}$ and $V_{2outT}$ are determined at time $T_{out}$ estimate, step 46, FIG. 3 and controller subsystem 20 calculates the total magnetic content (TMC) of the fluid as:

$$\text{TMC} = V_{1out} - V_{2out} \text{ (at time } T_{out} \text{ half way estimate)} \tag{1}$$

to account for the response of the coil due to temperature change, step 48, FIG. 3. $V_{1out}$ is where regression line 32b crosses $T_{out}$ estimate and $V_{2out}$ is where regression line 32a crosses $T_{out}$ estimate. Optimally, at time $T_{out}$ estimate, new best fit straight lines of the coil response data may be calculated in first and second zones (before and after $T_{out}$ estimate). The TMC may then be calculated based on the values of these new regression lines at $T_{out}$ estimate.

The system responds to thermal noise at a rate slower than the response to the total magnetic content of the sample fluid. By detecting when a thermal noise event occurs (e.g., the fluid container is being withdrawn from the sample chamber), the signal processing techniques described above allow the thermal noise to be accounted for in the thermal event.

In a further refinement, a second sensor subsystem is included proximate the top of the chamber, for example, LED emitter 32a, FIG. 1 and detector 23b. This sensor subsystem is used to detect when the container 16, FIG. 1, is being inserted into chamber 12. When detectors 23b and 22b, for example, no longer detects photons from emitters 23a and 22a, a container insert event time, $T_{in}$, shown in FIG. 4, step 60, FIG. 5, is set by controller subsystem 20, FIG. 1.

Figure 4:
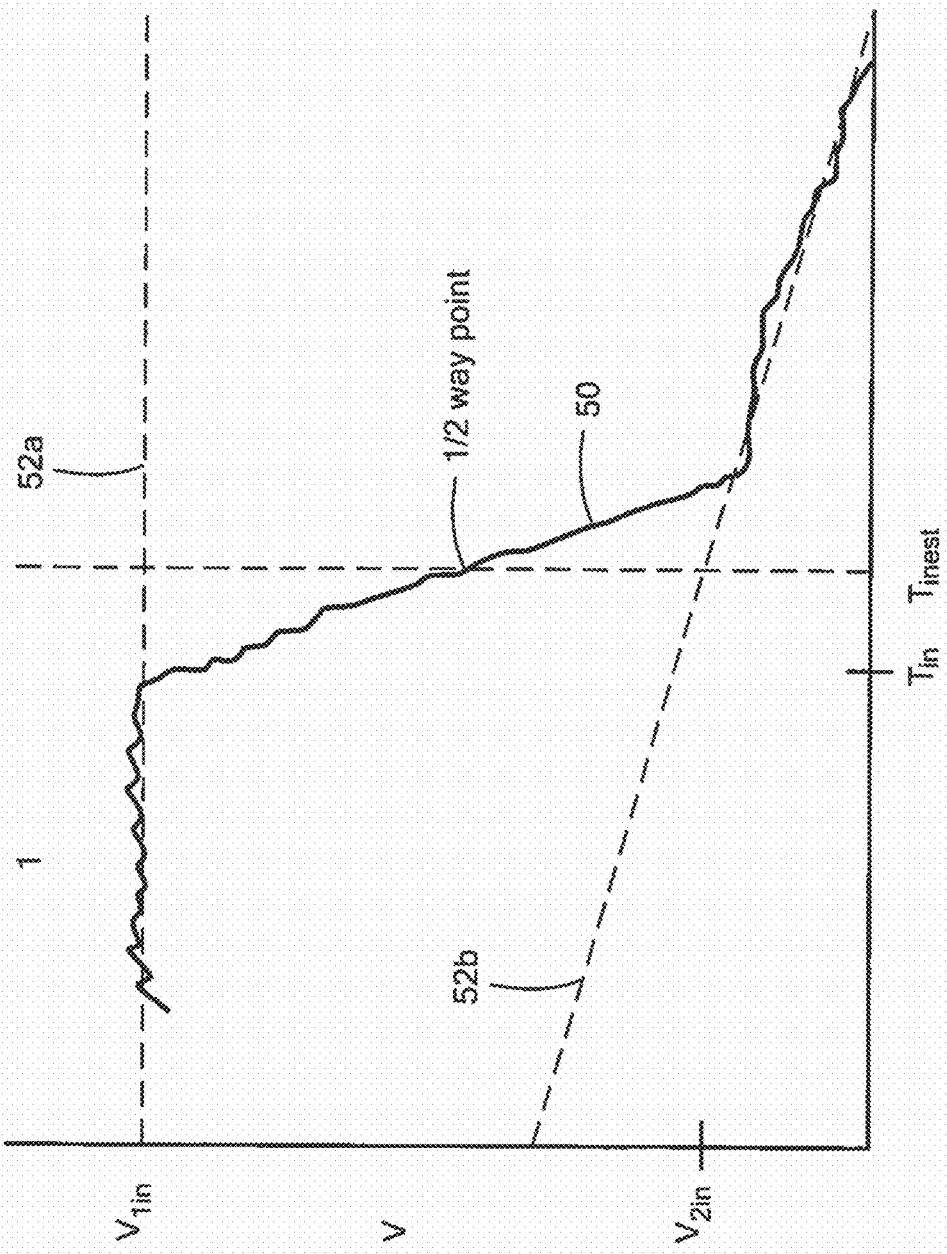
FIG. 4 is a graph showing an example of the response of the coil of FIG. 1 proximate the time the syringe container is introduced into the chamber of FIG. 1.

The response 50, FIG. 4, of the coil 10, FIG. 1, is further analyzed by the controller subsystem. In a window or zone of coil response data before $T_{in}$, a best fit straight line 52a is calculated by, for example, linear regression and in a window or zone of response data after $T_{in}$ another best fit straight line 52b is calculated. See step 62, FIG. 5.

Figure 5:
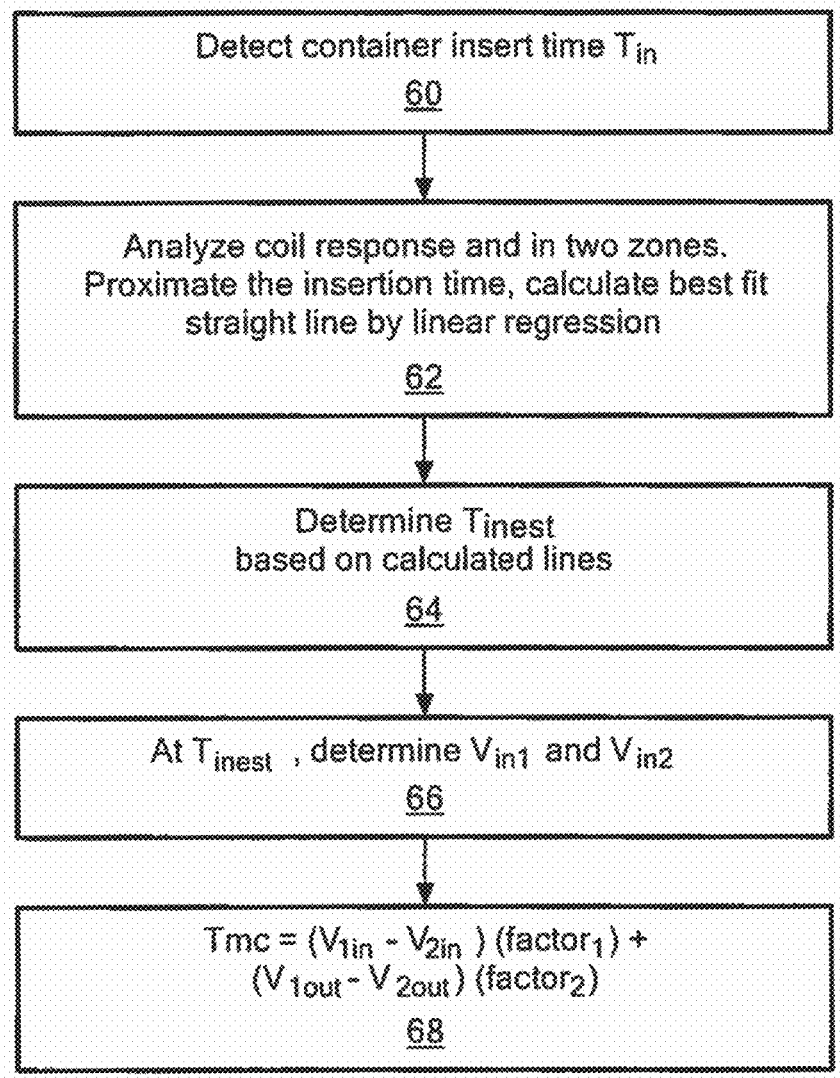
FIG. 5 is a flowchart depicting an example of the primary steps associated with the programming of the controller subsystem of FIG. 1 and also associated with a method in accordance with an example of the invention in order to more accurately determine the total magnetic content of the fluid.

As with $T_{out}$, $T_{in}$ may not be accurate due to the different ways a sample container may be inserted into the chamber so $T_{in}$ may be refined by the controller subsystem as shown at $T_{in}$ estimate in FIG. 4 which is at a time corresponding to the coil response half way between regression lines 52a and 52b, step 64, FIG. 5. New best fit regression lines may be calculated based on response data in a zone before $T_{in}$ estimate and after $T_{in}$ estimate. At $T_{in}$ estimate, the values $V_{1in}$, $V_{2in}$ of the regression lines 52a, 52b are determined, step 66, FIG. 5 and the controller subsystem 20, FIG. 1 calculates the total magnetic content of the fluid as the difference between $V_{1in}$ and $V_{2in}$ multiplied by a predetermined factor plus the difference between $V_{1out}$ and $V_{2out}$ multiplied by a different factor, step 68, FIG. 5. Factors in FIG. 5 may be 0.2 and factor$_2$ in FIG. 5 may be 0.8 as determined by testing of the system with known total magnetic content fluid samples. In practice, the insertion event tended to have higher errors and was thus weighted less than the removal event. The total mg/kg (ppm) of ferrous material may then be written as:

$$V_{1out} - V_{2out})(0.8) + (V_{1in} - V_{2in})(0.2) \qquad (2)$$

Though the nominal output voltage of the coil set is zero without a sample, in practice it is difficult to make identical coils, so there is typically a residual output.

In addition to sensing ferrous metals, the coil can detect the presence of non-ferrous metals as well. Rather than changing the inductance of the coil, non-ferrous metals change the apparent resistance of the coils. To take advantage of this, the system may measure the complex impedance of the coil rather than just its inductance. In addition to detecting non-ferrous metals, the coil's resistance can be used to measure the sample's temperature.

Figure 6:
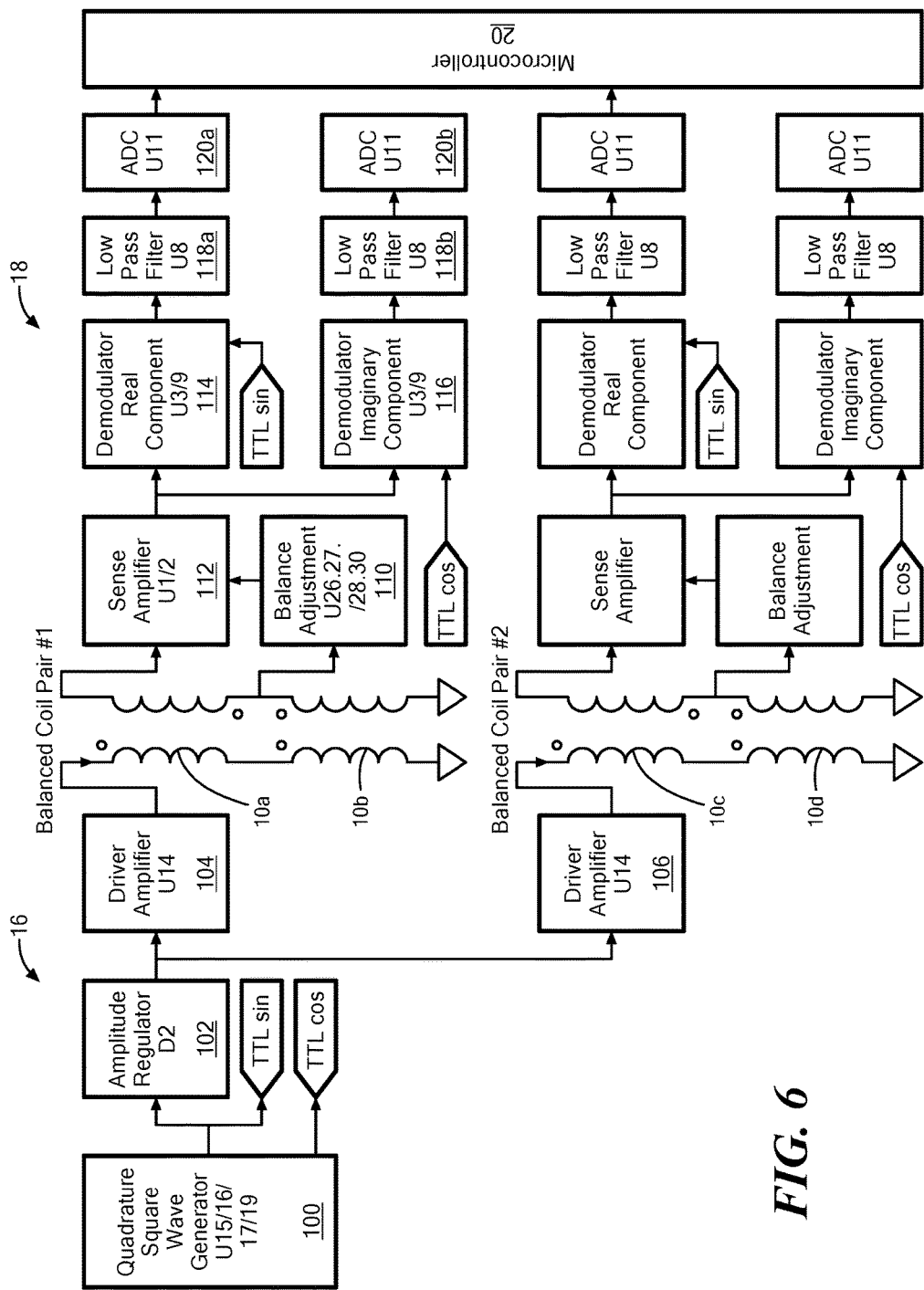
FIG. 6 is a block diagram showing the primary components associated with a magnetometer system which employs balanced coil pairs.

In one example, the coils 10a and 10b, FIG. 6 are excited with a 22 kHz pseudo-sine wave. The Quadrature Square Wave Generator 100 creates two digital square waves, TTLSIN and TTLCOS. In the Amplitude Regulator 102, TTLSIN is used to generate another square wave having extremely stable amplitude characteristics. This square wave is passed through a Low Pass Filter within amplifier 102 which attenuates the harmonics of the square wave. Since the harmonics are not completely removed, the waveform is not exactly sinusoidal, thus the label pseudo-sine. This signal is fed to the Driver Amplifier 104 which changes the voltage and provides high current drive capability to drive the coil pair. Coil pair 10c and 10d has its own amplifier 106 which may have a different gain to provide a different drive voltage to the second coil pair.

The Drive Amplifier connects to the series pair of coils. As noted above, the coil pair may be imbalanced and generate a non-zero output with the sample cell empty. The Balance Adjustment circuit 110 cancels this imbalance by injecting a small adjustable AC current into the junction at the output of the coil set. The imbalance may have any phase, so two independently adjustable currents are injected.

As described above, the coil primaries are in series and the secondaries are in anti-series. This in combination with the imbalance adjustment provides an output signal that is typically in the range of 0~1 millivolt peak-to-peak. The Sense Amplifier 112 has a gain in the low thousands, and in addition provides several stages of high- and low-pass filtering. The output of Sense Amplifier 112 is demodulated via demodulation 114 using, an inverting amplifier and an analog switch. The inverting amplifier has a gain of −1, producing a 180° phase-shifted version of the sense amplifier output. The analog switch is driven by the TTLSIN signal, which is a square wave at the same frequency as the amplifier output. When TTLSIN is high, the amplifier output is selected, while when TTLSIN is low, the inverted output is selected. Thus an AC signal from the amplifier, having no DC component, is converted to a pulsating DC level that is proportional to the AC amplitude.

A second demodulator 116 is used to detect signals that are not in phase with TTLSIN and would not produce an output from the first demodulator. It works the same way as the first demodulator but is driven by TTLCOS, which is 90° out of phase with TTLSIN. The output of the two demodulators provide a real and imaginary component of a complex number that describes the magnitude and phase of the Sense Amplifier output.

Low Pass Filter 118 is used to eliminate the pulsations in the outputs of the Demodulators. It may be a two-pole filter with a 100 Hz knee and a DC gain of 2.

The ADC 120 converts the output of the Low Pass Filter. It is preferably a 16-bit, 8 channel SAR type ADC with an internal 2.5V reference and a signal range of 0-2.5V. The ADC converts all four Filter outputs at a rate of 500 samples/second for each channel (total sample rate of 2000 samples/second). Since it is a single ADC with a multiplexer, the acquisition is not simultaneous. The skew is made as small as is convenient based on programming considerations, simply by taking each of the four samples in succession.

The microcontroller 20 receives the ADC samples and formats the four 16-bit values into a comma separated ascii stream terminated with <cr><lf>. The stream is sent out of the USB port with no handshaking. Transmission begins upon powerup of the microcontroller. All inputs to the USB port are ignored.

The Quadrature Square Wave Generator 100 generates a two-bit binary gray code. The sequence is 00, 01, 11, 10. Each state persists for about 11.4 microseconds, and the complete sequence repeats every 45 microseconds. The result is two pulse trains (TTLSON and TTLCOS), each having a frequency of 22 kHz and a duty cycle of 50%, and are thus square waves. There is a 11 microsecond delay between the two signals, equivalent to a phase shift of 90 degrees. The outputs have normal CMOS output levels. The Amplitude Regulator 102 takes the square wave output from the Quadrature Square Wave Generator and produces a waveform having the same timing but having well-defined high and low voltage levels. This is done by creating two DC voltages, approximately 2.5 and 7.5V, in which the voltage difference between these two voltages is precisely controlled to be 5V. An analog switch alternates between these two voltages, producing a square wave with precisely controlled amplitude of 5V p-p.

The Low Pass Filter in amplifier 102 is three-pole Sallen-Key filter with a gain of 1.5 and a −3 db point of about 15 kHz. This filter attenuates the harmonics of the input square wave, making the waveform close to a sine wave.

The Driver Amplifiers 104 use high-power operational amplifiers in an inverting configuration. Their gain is 1.47, but this can be tailored for different applications. In their standard configuration, the output voltage is about 8V p-p.

The Balance Adjust network consists of two digital potentiometers that are used to adjust the output of the coils so that the output is near zero when no sample is introduced into the cell. To generate the signals for balancing, the voltage at the junction of the two secondaries is used. This voltage is about 10 Vp-p, and is reduced to 3-4 Vp-p by balance adjustment 110. Balance adjustment also generates a copy of the signal that is phase shifted by 180 degrees. A digital potentiometer is fed by these two signals and thus can generate any voltage between these two levels, including zero. This voltage is fed to the coil through a 10K resistor. The voltage from balance adjustment 110 is phase shifted by about 90° and injected in the same way as described above.

The Balance Coil is described elsewhere. In short it consists of two transformers with the primaries connected in series and the secondaries connected in anti-series. It is excited by the 8V p-p drive voltage and its output is nominally zero under balanced conditions (no sample in cell).

Figure 7:
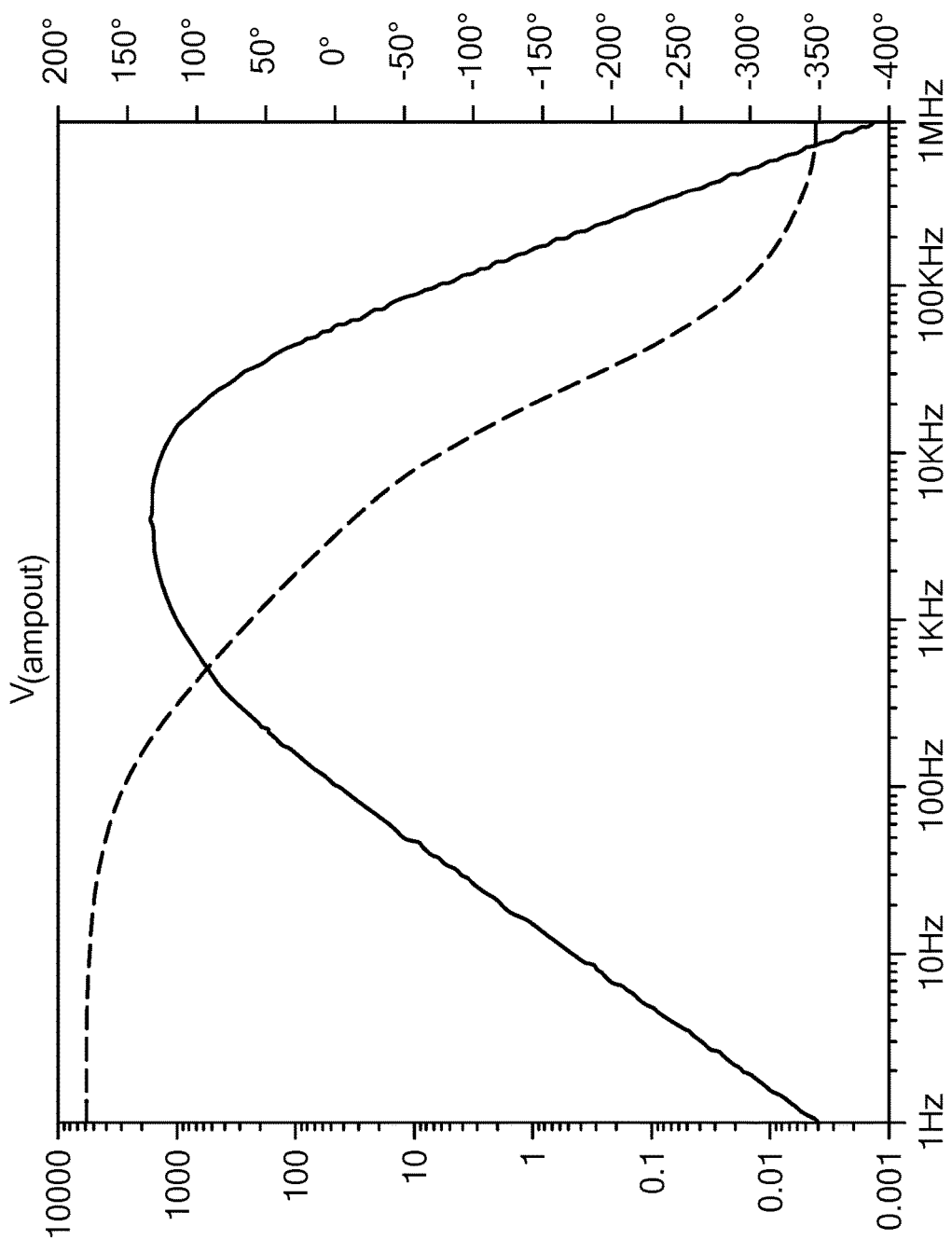
FIG. 7 is a graph showing the overall gain and phase of the output of the electronics section of FIG. 6.

The sense amplifier 112 is a three-stage high gain amplifier having a gain of about 1000 and a band-pass characteristic. The first stage is a low-noise amplifier suited to amplifying the low-impedance output of the sense coils. Its gain is 83 and it has a low-pass characteristic. The second stage is a gain of 8.3 bandpass, and the third stage is a gain of 1.6 bandpass. The overall gain and phase are shown in FIG. 7.

Each channel has two demodulators, one for the imaginary component and one for the real component. Note that because of phase shifts in the circuit, "real" and "imaginary" do not correspond to ferrous and non-ferrous signals, and further processing will be done in firmware later to create the required signals.

Each demodulator consists of an inverting amplifier with a gain of −1, followed by an analog multiplexer. Each multiplexer alternately connects its output to either the input or the output of the inverting amplifier. The multiplexer's control input is driven by the output of the Quadrature Square Wave Generator. The output of the demodulator is thus sensitive to inputs at the frequency of the drive voltage, and rejects other frequency components in the signal. It is also phase sensitive, rejecting signals that are phase shifted by 90 degrees from the control signal. Note that the demodulator will also respond to odd harmonics of the drive signal, but these harmonics are highly attenuated by the sense amplifier.

The Low Pass Filter 118 is preferably a MFB (Multiple Feedback) low-pass filter having a gain of 2 and a −3 db point of about 100 Hz. It smoothes the output of the demodulator to produce a ripple-free waveform.

The ADC 120 converts the output of the filter to digital form. It is preferably a 16-bit SAR (Serial Approximation Register) converter.

The Microcontroller 20 takes the digital values from the four ADC's, formats them, and transmits them through a serial port.

Figure 8:
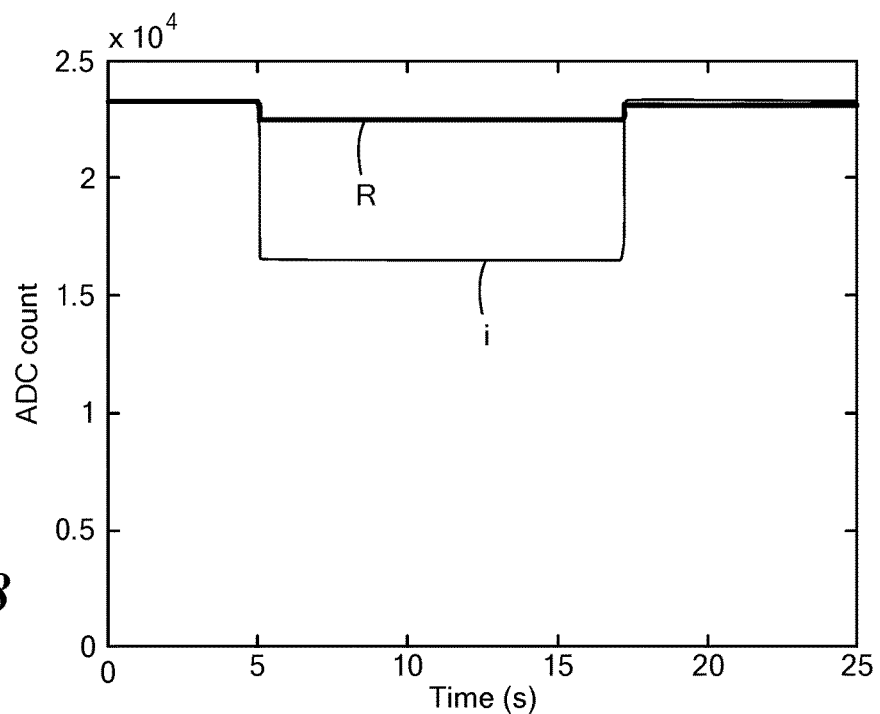
FIG. 8 is a plot showing an example of the real and imaginary outputs of the system during the insertion and removing of a sample.
Figure 9:
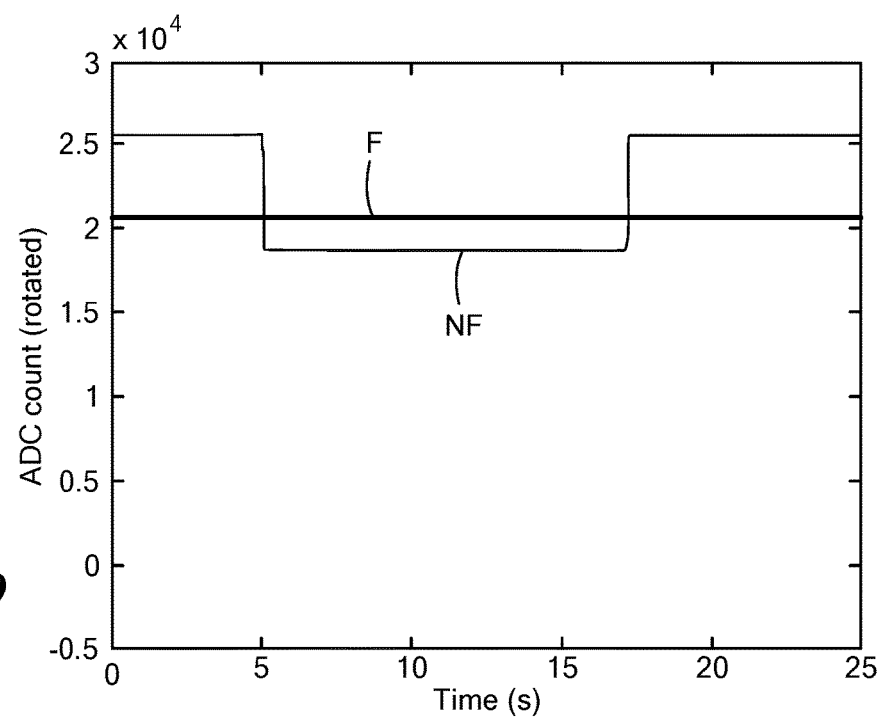
FIG. 9 is a plot showing the rotation of the signals of FIG. 8 to separate the ferrous channel signal.
Figure 10:
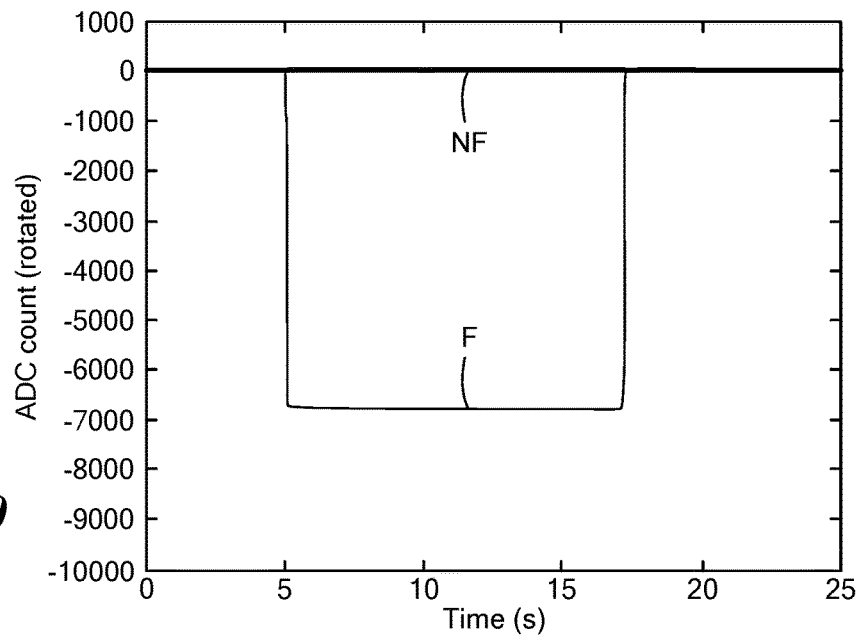
FIG. 10 is a graph showing the signals of FIG. 9 clamped.

The plot of FIG. 8 shows the real (r) and imaginary (i) outputs of the system during the insertion and removal of a sample of about 500 ppm. Note that both channels respond to the ferrous material being introduced. Rotating the complex vector (see FIG. 9) cleanly separates the ferrous signal F from the non-ferrous signal NF. Clamping the signals removes the starting value as shown in FIG. 10.

In the example above, the sample was at the same temperature as the coil. If the sample is at a different temperature from the coil, heat flow between the sample and coil produce distortions that must be accounted for.

Figure 11:
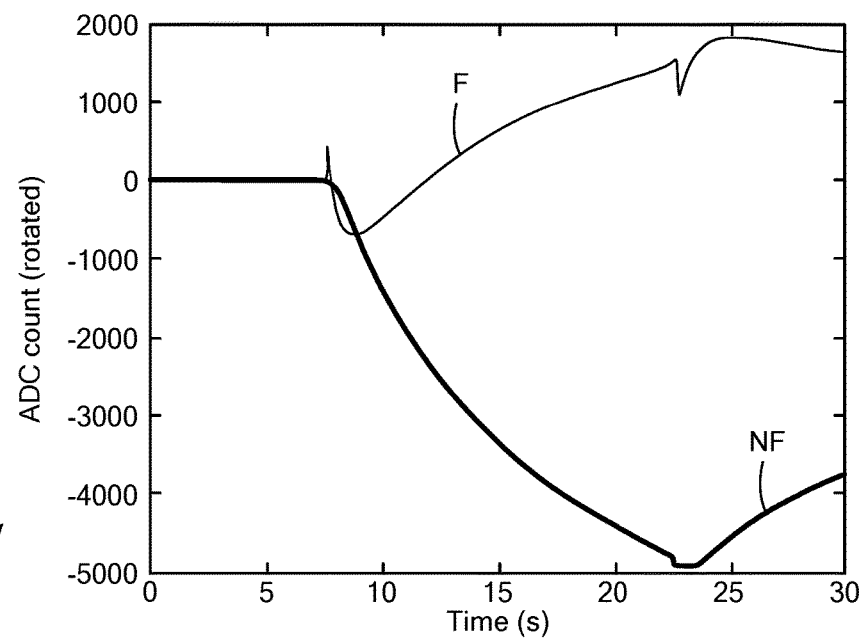
FIG. 11 is a plot showing an example of the response of a clear oil (no ferrous content) sample.

The plot of FIG. 11 shows an example of clear oil (no ferrous content). From the previous example one would expect both the ferrous and non-ferrous signals to be zero throughout the insertion and removal of the sample. Clearly this is not the case. The first feature to notice is that there is an immediate response in the ferrous channel of about 400 counts at insertion and removal, even though there is no ferrous material in the sample. Also note that this response is in the opposite direction (increasing) compared to the ferrous signal seen in the first example (decreasing). This is caused by the fact that the sample has a dielectric constant, which for a typical oil sample might be about 2.1. The dielectric constant increases the capacitance in the coil, giving a response that is the opposite of an increase in inductance (capacitive and inductive reactance are 180° out of phase).

Next note that there is a delayed response in the ferrous channel. This response is due to changes in the coil that are sensitive to temperature, such as thermal expansion of the bobbin and windings. These changes will of course have complex dynamic responses as the temperature disturbance propagates through the structure of the coil.

In the non-ferrous channel, there is a different response. Upon removal, the disturbances are reversed.

Figure 12:
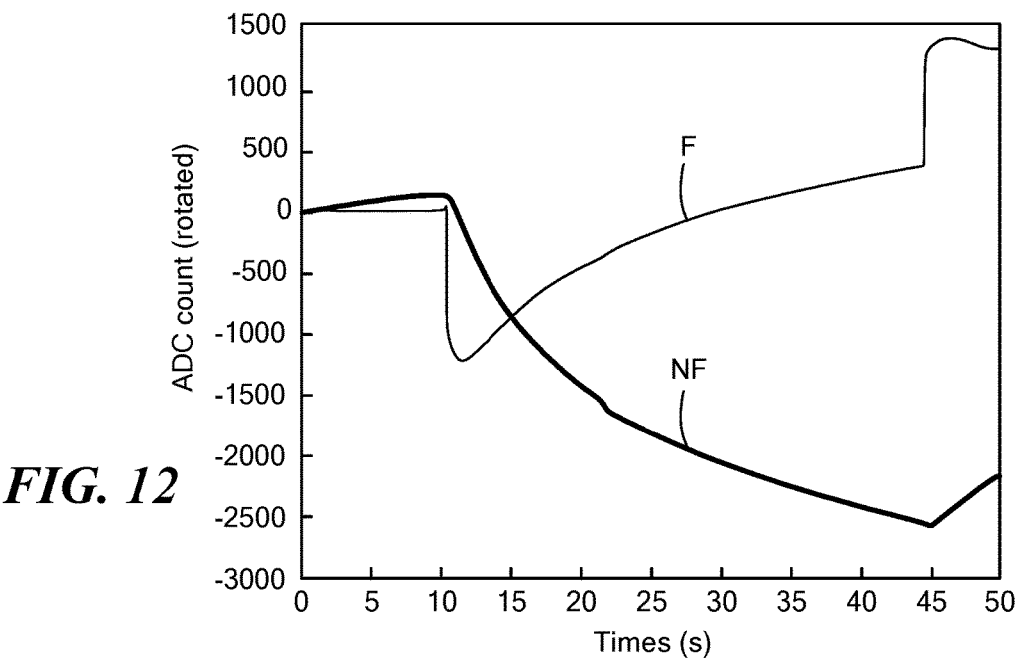
FIG. 12 is a plot showing the response of the system to a sample of 100 ppm ferrous content oil.
Figure 13:
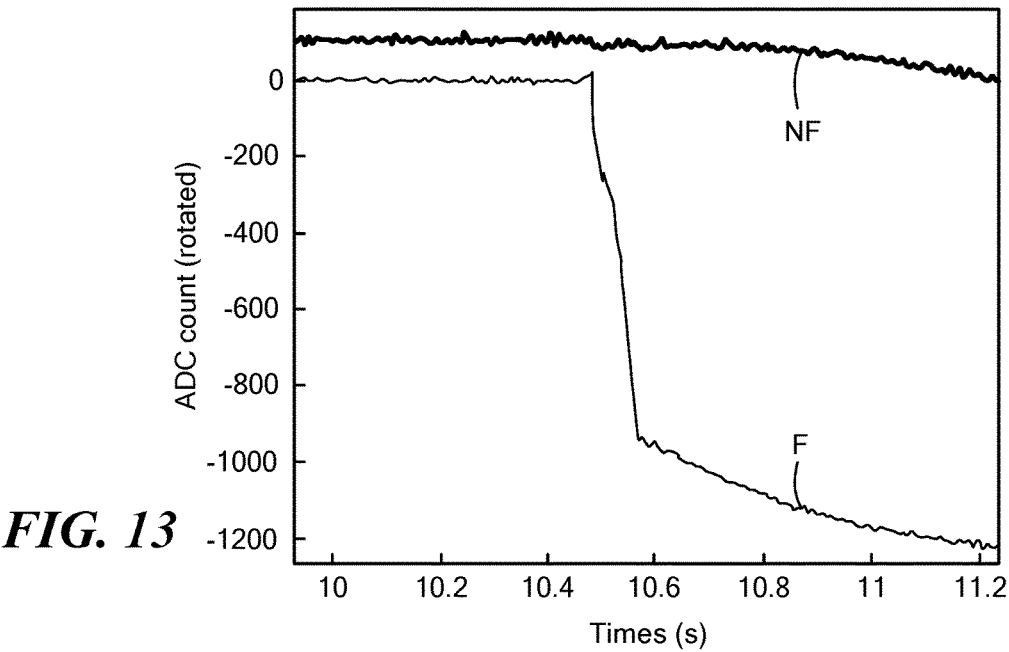
FIG. 13 is an enlarged view of the coil response at a sample insertion event of FIG. 12.

A typical system response to a sample of 100 ppm ferrous content oil is shown in FIG. 12. As expected, the immediate response of the ferrous channel is negative, indicating that the ferrous signal is larger than the dielectric signal. An enlarged view of the insertion event is shown in FIG. 13.

Note that it is easy for a human observer to identify the insertion, it is not so simple to find it in a program. For this reason, two sensor subsystems are provided, one at the top of the coil and one at the bottom a shown in FIG. 1. From these two signals, the time of insertion can be estimated. Note that the insertion time is not a well-defined quantity, as the insertion motion of a human operator is not known in advance. The example above shows non-uniform motion.

Figure 14:
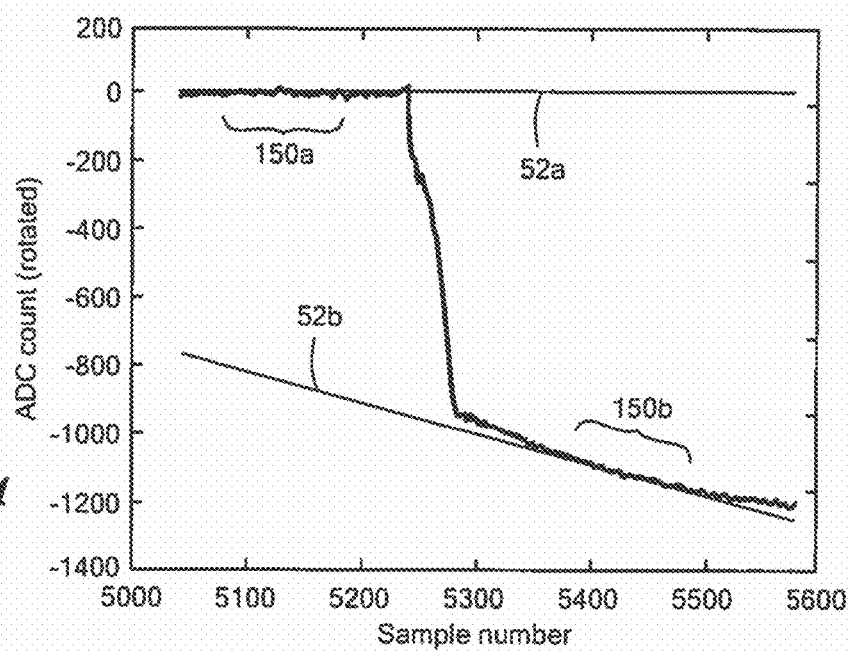
FIG. 14 is a plot showing calculation of best fit straight lines in two zones before and after the insertion event.

With a rough estimate of insertion time, two zones are defined before and after the insertion. The first zone is before the top sensor was noted, and the second zone is after the bottom sensor is noted. In each zone, a best fit straight line is calculated by linear regression. In the plot of FIG. 14, the fitting zones are at 150a and 150b and the regression lines are at 52a and 52b.

Figure 15:
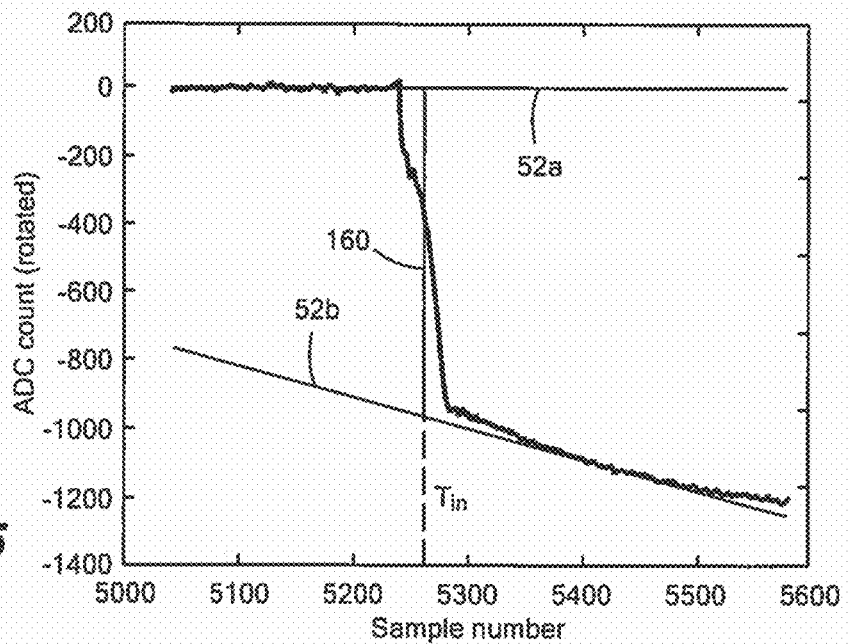
FIG. 15 is a graph showing how the values of the regression lines are calculated at the time of the insertion event and how the difference between these values is taken as a ferrous measurement.

From the sensor subsystem signals, the estimated insertion time $T_{in}$ is known. The values of the regression lines 52a and 52b are calculated at that time, and the difference between these values is taken as the ferrous measurement. In the plot of FIG. 15, the vertical line 160 connects these two points, and the height of the line equals the total ferrous content measurement.

Figure 16:
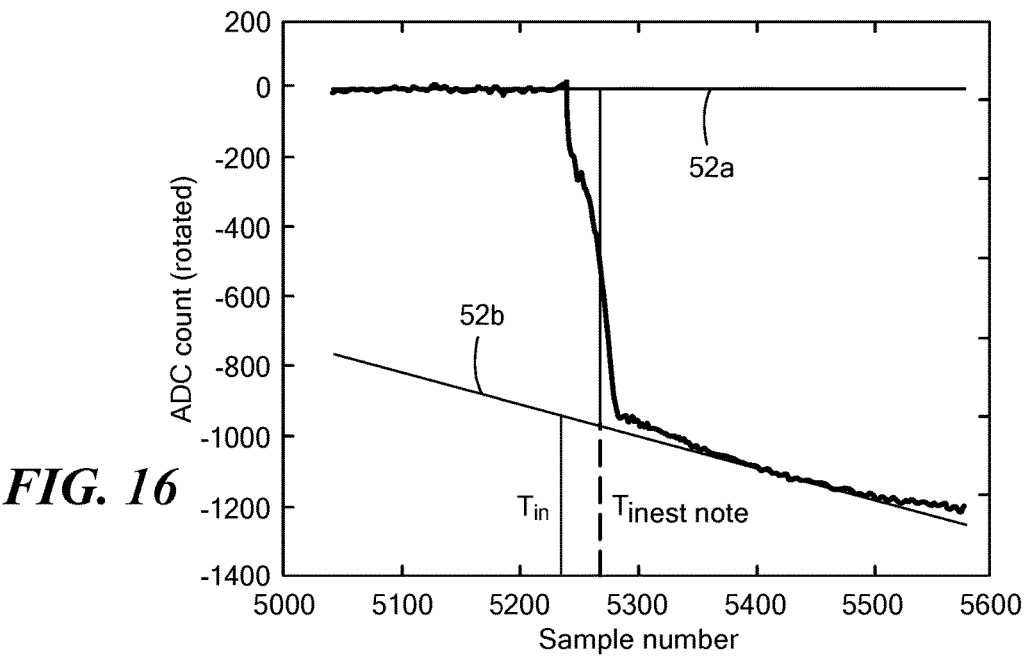
FIG. 16 is a graph showing how the insertion time estimate is improved.

The estimated insertion time may not be accurate, and any error in this value will create an error in the measurement. In the plot of FIG. 15, estimating the insertion too early will reduce the measurement, and too late will increase it. The insertion time estimate may be improved by picking a time at which the ferrous signal is at a level that is halfway between the regression lines. This improvement is shown in FIG. 16.

Figure 17:
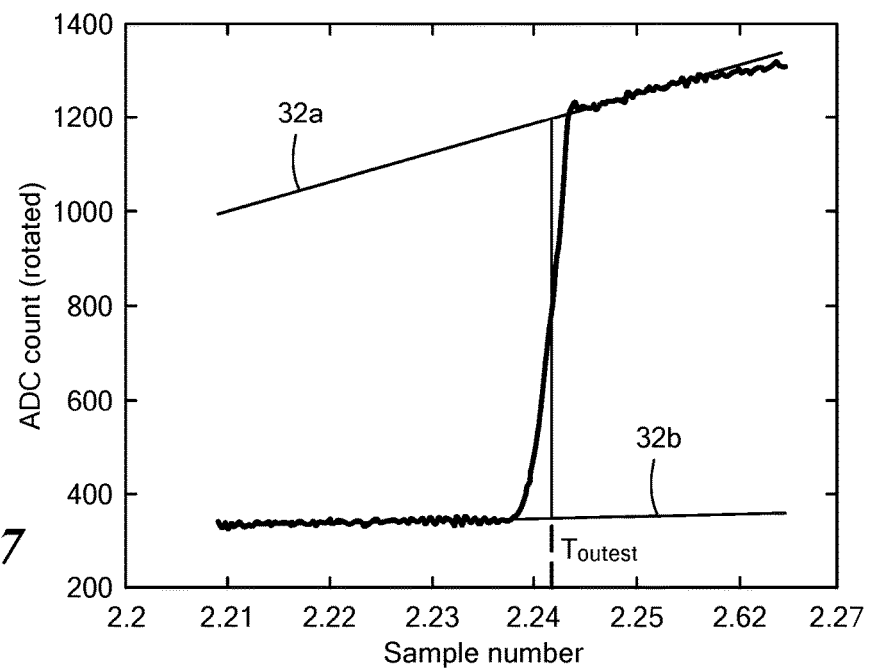
FIG. 17 is a graph showing the response of the system and the signal processing determinations as a fluid sample is being removed from the system.
Figure 18:
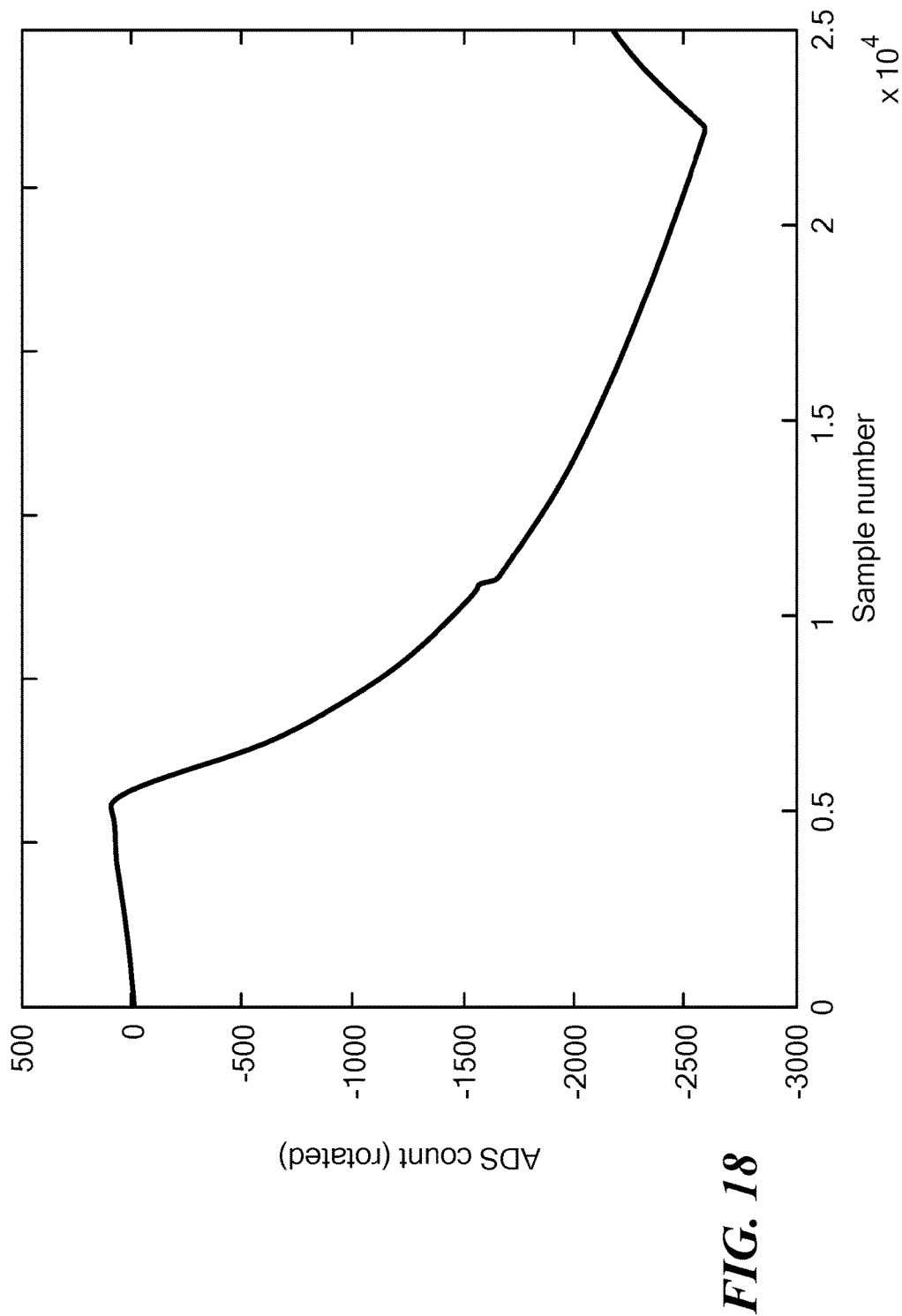
FIG. 18 is a graph showing the response of the non-ferrous channel of the sensing electronic section in order to estimate the temperature difference between the sample and the coil.

The previous examples show a measurement being made at the time of insertion. The same techniques can be used at time of removal, and yield the plot of FIG. 17.

Two more measurements ("amount1", "amount2") can be taken from the non-ferrous channel. Since this sample does not have significant ferrous content, the non-ferrous channel can be used to estimate the temperature difference between the sample and the coil. This is done by calculating the difference between the slopes of the regression lines before and after insertion (amount1) and removal (amount2).

Note that the measurements shown above may be all in units of ADC counts. As a result they do not represent ferrous content. An equation is required to convert from ADC counts to Ferrous PPM.

$$PPM = step1 * step1fac + step2 * step2fac + \\ amount1 * amount1fac + amount2 * amount2fac + ofst \quad (3)$$

The first line in equation (3) does the basic conversion from ADC counts to PPM. The second line adds a correction for the temperature difference between the sample and the coil. The third line adds an offset to compensate for the dielectric effect.

Note that for step and amount, separate factors are included for insertion and removal. This gives the ability to weight these two events based on the observed quality of the measurements. In practice, insertion tends to have higher errors and is thus weighted less than removal.

For the 100 ppm sample discussed above, the values and factors are shown in Table 1 below.

TABLE 1

| Measurement | Value | Factor | Value | Product |
|---|---|---|---|---|
| step1 | −969.6809 | step1fac | −0.0049 | 4.7223 |
| step2 | −847.3919 | step2fac | −0.0550 | 46.6095 |
| amount1 | 0.5652 | amount1fac | 42.7814 | 24.1801 |
| amount2 | −0.2461 | amount2fac | 62.5125 | −15.3843 |
|  |  | offset | 40.1956 | 40.1956 |

Calibration is performed by a spreadsheet that calculates this equation for a number of measurements taken with a variety of known PPM levels and temperatures. The factors are developed by minimizing the least-squares error for all of the samples using, for example, a Newton's method search. These parameters are then saved in the controller subsystem so a real-time readout may be provided.

The firmware of the controller subsystem was first developed in Matlab, then converted to C for insertion into the controller subsystem. The description below refers to an example of the Matlab code.

The custom m-files used in the measurement are:

| File Name | Description |
|---|---|
| measureferrous.m | Top level measurement function |
| shiftphase.m | Rotates the phase vector of the raw data and delivers ferrous and nonferrous channels |
| clamp.m | Forces the starting value of both channels of a data record to zero |
| sensorsNew.m | Cleans up the sensor data and delivers unambiguous in and out times |
| transTime.m | Calculates the transition times of insertion and removal |
| FindSteps.m | Removes thermal effects from data and delivers step1 and step2 |

Data Structure

The data used by the Matlab program includes of four values, each sampled at 500 Hz.

They are:
1. Real channel
2. Imaginary channel
3. Upper sensor
4. Lower sensor

Typical values would be:

| | | | |
|---|---|---|---|
| 23159 | 23254 | 45790 | 43878 |
| 23149 | 23252 | 45795 | 43879 |
| 23158 | 23255 | 45793 | 43881 |
| 23161 | 23259 | 45794 | 43879 |
| 23155 | 23263 | 45797 | 43879 |
| 23151 | 23258 | 45795 | 43875 |
| . | . | . | . |
| . | . | . | . |
| . | . | . | . |

A typical test duration would be 20 seconds, so there would be 500*20=10000 rows of data.

measureferrous is the top level measurement function and calls all of the other functions. At line 14, the raw data file from the magnetometer is stripped of the sensor channels and saved as "magdata". At line 15, magdata is then rotated by shiftphase.m, by an amount "phase". The phase shift required is a function of the individual electronics and coils in a given unit. A typical value is 11 degrees. The rotated magdata is then clamped by clamp.m so that both channels start at zero. At line 21, sensorsnew.m finds the transition times of the upper and lower sensors. At line 23, transTime.m finds the estimated insertion and removal times based on the sensor data. It also finds amount1 and amount2 from the non-ferrous channel values. At line 26, FindSteps.m finds the step1 and step2 values, based on magdata and the sensor in and out times.

The shiftphase module shifts that phase of the magnetometer data so that the two output channels represent ferrous and non-ferrous data. At line 9, to rotate the raw magnetometer data to ferrous and non-ferrous channels, the data is first converted to a complex data type. Then the complex value is multiplied by a unit vector having an angle of "degrees". The resulting complex data is then converted back to real and imaginary components. The real component is the non-ferrous channel, the imaginary component is the ferrous channel.

The clamp forces the average of the first second of output data to zero. At line 8, the first 500 values (1 second of data) of the input data are averaged. In lines 10 and 11, these averages are subtracted from the input data.

A sense value of zero means that a broken beam generates a lower voltage. At lines 18 and 19, "top" and "bottom are extracted from the raw data, representing the data from the top and bottom sensors, respectively. At line 26, "sense" is applies by negating the sensor data if the sense value is 0. In the next section, deciles of voltage are determined. Decile1 is 0.1 times the number of elements in the sensor voltage array, and decile9 is 0.9 time the number of elements. For instance, if the record is 10,000 elements long (20 seconds), decile1 would be 1000 and decile9 would be 9000.

Lines 39-48 are not used. In line 53, the top array is sorted. In our example, we would then find the $1000^{th}$ and $9000^{th}$ values in the sorted list. Our threshold would be set to the mean of these two values.

Imagine a sensor having two distinct but unknown values, say 3 and 4 volts, with other values occurring during transitions. A normal insertion sequence would have the sample out for the first 5 seconds, in for the next 10 seconds, and out for the next 5 seconds. The sorted list should then have something less than 5000 samples of 3V, then a short list of intermediate values, then something less than 5000 samples of 4V. The $1000^{th}$ value should be 3V and the $9000^{th}$ value should be 4V. The threshold would then be 3.5V. This method is tolerant of wide variations in sample timing, as long as the total in or out times are not less than 10% of the length of the record.

In line 58, applying the threshold to the top array, we would have a two-level result firstTop represents the first time (sample number) that the top sensor exceeds the threshold, and thus represents the first time that the syringe breaks the top sensor's beam. lastTop is the last time. midTop is halfway between, and represents a time that with high probability the syringe is in the coil. At line 62-66, the analogous calculations are made for the bottom sensor. For firstBot, only part of the voltage array is used, that part spanning from the first element in the array to midTop. This finds the sample number of the last time that the voltage drops below the threshold.

Lastbot is calculated using an array that goes from midtop to the end of the voltage array. The value is the first sample number that falls below the threshold. Line 68 to 103 are obsolete. Line 106-110 take firstTop and firstBot, and using them, create new limits out(1) and in(1). firstTop represent the first occurrence of a threshold transition, while out(1) represents the last occurrence of a threshold transition. firstBot represents the last occurrence of a threshold transition, while in(1) represents the first occurrence of a threshold transition. Lines 113-118 perform the same function for out(2) and in(2).

The transTime function calculates amount1 and amount2, which indicate the temperature difference between the sample and the coil. At line 24, CH1 and CH2 are extracted from magdata. Four zones are defined around the insertion time. Zone1 is 300 samples (0.6 seconds) long and extend from 400 samples before out(1) to 100 samples before out(1). Zone2 is also 300 samples and extends from 500 samples after in(1) to 800 samples after in(1). Zone2 is farther removed from the sensor transition because there is a thermal delay in the signal to be analyzed. Zone3 and zone4 are analogous to zone1 and zone2 but apply to the removal time. At line 34, in each zone, channel 1 (the non-ferrous channel) is fit with a linear regression line. Lines 41-48 are no longer used. At line 49, the amounts are calculated as the difference between slopes of the regression lines. Zone1 and zone2 are used for insertion; zone3 and zone4 are used for removal. Lines 52 and 53 are no longer used.

The FindStep function finds the ferrous signal while rejecting the thermal signature. At line 20, CH1 and CH2 are extracted from magdata. Lines 23-28 define zines for line fitting, as was done in transTime, but the zones are different. Each zone is 100 samples long. Zone1 runs from 100 samples before out(1) to out(1). Zone2 runs from in(1)+100 to in(1)+200. The delays are different because before the upper sensor is broken, it is safe to use the data for fitting. After the bottom sensor is broken, there can still be some "fiddling" that would affect the signal. Zone3 and zone4 are treated analogously.

At line 31 the linear regressions are done. Lines 36 and 37 calculate the estimated insertion and removal times, based on the sensor signals. Line 48 finds the values of the two line fits at the estimated insertion time, and returns the mean of those two points. Lines 50-61 find the sample number at which the ferrous signal is closest to the mean value from line 48. This is the revised insertion time. Line 63 calculates the ferrous value (step1), which is the difference between the two regression lines at the revised insertion time. Lines 67-81 make the same calculation for the extraction.

| | Matlab Code |
|---|---|
| 1 | function [step1, step2] = measureferrous(rawdata, phase); |
| 2 | |
| 3 | % [steps1, steps2] = measureferrous(rawdata, phase); |
| 8 | % rawdata is the 4-column data delivered by the magnetometer |
| 9 | % phase is the know phase shift for the magnetometer |
| 10 | % filter is a matrix in the form of [numd; dend] |
| 11 | % advance is the delay in samples used to optimize the filter |
| 12 | % and is normally 500. |
| 13 | |
| 14 | magdata = rawdata(:,1:2); |
| 15 | magdata = clamp(shiftphase(magdata, phase)); |
| 16 | |
| 20 | |
| 21 | [out, in] = sensorsNew(rawdata); |
| 22 | |
| 23 | [times, amounts] = transTime(magdata, in, out); |
| 25 | |
| 26 | [step1, step2] = FindSteps(magdata, in, out); |
| 1 | function shifted = shiftphase(raw, degrees); |
| 2 | |
| 3 | % Shift phase of a record from magnetometer |
| 4 | % |
| 5 | % Usage: shifted = shiftphase(raw, degrees); |
| 6 | % |
| 7 | % Raw record is two columns, real im |
| 8 | |
| 9 | cplx = raw(:,1) + i* raw(:,2); |
| 10 | crot = cplx* exp(i*degrees*pi/180); |
| 11 | shifted = [real(crot) imag(crot)]; |
| 1 | function clamped = clamp(raw); |
| 2 | |
| 3 | % clamped = clamp(raw); |
| 4 | % |
| 5 | % clamps a spectro magnetometer record to zero |
| 6 | % Based on the first 500 samples (1 second) |
| 7 | |
| 8 | offsets = mean(raw(1:500, :)); |

| Matlab Code |
|---|

```
9
10      clamped (:,1) = raw(:,1) − offsets(1);
11      clamped (:,2) = raw(:,2) − offsets(2);
1  function [out, in] = sensors new (rawdata)
2
3
7
8  sense = 0;
17
18      top = rawdata(:, 3);
19      bot = rawdata(:,4);
20
21
22      % Find the levels and create thresholds
25
26      if sense == 0;
27          top = −top;
28          bot = −bot;
29      end
30
31
32
33
34      decile1 = 0.1 *round(length(top));
35      decile9 = 0.9 *round(length(top));
36
38
39      startvalue = top(1);
44
45      top1 = top > startvalue + 1000;
46      top2 = top < startvalue − 1000;
47      top3 = [0; abs(diff(top1)) & abs(diff(top2))];
48      top = (top1 | top2) & ~top3;
49
50
52
53      tops = sort(top);
54      threshold1 = mean([tops(decile1) tops(decile9)]);
55
57
58      firstTop = min(find(top > threshold1)); % First occurence of top sensor interrupt
59      lastTop = max(find(top > threshold1));% Last
60      midTop = round(mean([firstTop lastTop])); % sample # of the middle
61
62      bots = sort(bot);
63      threshold2 = mean([bots(decile1) bots(decile9)]);
64
65      firstBot = max(find(bot(1:midTop) < threshold2));
66      lastBot = min(find(bot(midTop:end) < threshold2)) + midTop − 1;
67
68      % Quality control measures
69
70      % Set limits on insertion and removal times
71
72      minPrefix = 500 * 4; % Samplerate * seconds
73      maxTransition = 500 * .2;
74      minDwell = 500 * 8;
75      minSuffix = 500 * 8;
76
77      prefix = firstTop; % Amount of acquisition time before the sample is inserted
78      trans1 = firstBot − firstTop; % How long did it take to inser the sample
79      dwell = lastBot − firstBot; % How long was the sample fully inserted
80      trans2 = lastTop − lastBot; % How long did it take to remove the sample
81      suffix = length(top) − lastTop; % How long did we acquire after removal
82
83      if prefix < minPrefix
84          disp('prefix too short')
85      elseif trans1 > maxTransition
86          disp('transition #1 too long')
87      elseif trans2 > maxTransition
88          disp('transition #2 too long')
89      elseif dwell < minDwell
90          disp('dwell time too short')
91      elseif suffix < minSuffix
92          disp('suffix time too short')
93      end
94
```

-continued

| | Matlab Code |
|---|---|
| 95 | % Create limits for signal averaging |
| 96 | |
| 97 | % eliminate some samples for settling and residual motion |
| 99 | out = [firstTop lastTop]; |
| 100 | in = [firstBot lastBot]; |
| 101 | |
| 102 | outold = out; |
| 103 | inold = in; |
| 104 | |
| 105 | % Now change in % out to refer to inner transitions |
| 106 | start = firstTop−1; |
| 107 | finish = firstBot +1; |
| 108 | range1 = start:finish; |
| 109 | out(1) = start + max(find(top(range1) < threshold1)); |
| 110 | in(1) = start + min(find(bot(range1) > threshold2)); |
| 111 | |
| 112 | |
| 113 | start = lastBot −1; |
| 114 | finish = lastTop +1; |
| 115 | range2 = start:finish; |
| 116 | |
| 117 | out(2) = start + min(find(top(range2) < threshold1)); |
| 118 | in(2) = start + max(find(bot(range2) > threshold2)); |
| 119 | |
| 1 | function [times, amounts] = transTime(magdata, in, out); |
| 2 | |
| 3 | % Transition time from thermal data |
| 4 | % |
| 5 | % Usage: [times, amounts] = transTime(magdata, in, out); |
| 6 | % |
| 7 | % times is a 2-element vector having the caculated |
| 8 | % transition times based on the thermal data. |
| 9 | % |
| 10 | % amounts is the relative strength of the thermal step |
| 11 | % and is based on the change in slope of the thermal channel |
| 12 | |
| 13 | |
| 14 | |
| 22 | |
| 23 | |
| 24 | CH1 = magdata(:, 1); |
| 25 | CH2 = magdata(:, 2); |
| 26 | |
| 27 | %Note zones are different from the ones used in FindSteps |
| 28 | |
| 29 | zone1 = (out(1)−400 : out(1)−100)'; |
| 30 | zone2 = (in(1)+500 : in(1)+800)'; |
| 31 | zone3 = (in(2)−400 : in(2)−100)'; |
| 32 | zone4 = (out(2)+500 : out(2)+800)'; |
| 33 | |
| 34 | p1 = polyfit(zone1, CH1(zone1), 1); |
| 35 | p2 = polyfit(zone2, CH1(zone2), 1); |
| 36 | p3 = polyfit(zone3, CH1(zone3), 1); |
| 37 | p4 = polyfit(zone4, CH1(zone4), 1); |
| 38 | |
| 39 | % Find the crossings. m1x+b1 = m2x+b2; x = (b2−b1) / (m1−m2) |
| 40 | |
| 41 | X1 = (p2(2) − p1(2)) / (p1(1) − p2(1)); |
| 42 | X2 = (p4(2) − p3(2)) / (p3(1) − p4(1)); |
| 43 | |
| 44 | delay =160; |
| 46 | |
| 47 | times = [X1 X2]; |
| 48 | times = times − delay; |
| 49 | amounts = [p1(1)−p2(1) p3(1)−p4(1)]; |
| 50 | |
| 51 | |
| 52 | midpoint1 = round(mean([out(1) in(1)])); |
| 53 | midpoint2 = round(mean([out(2) in(2)])); |
| 54 | |
| 58 | |
| 1 | function [step1, step2] = FindSteps(magdata, in, out); |
| 2 | |
| 3 | % Remove thermal effects from magnetometer data |
| 4 | % |

-continued

| | Matlab Code |
|---|---|
| 5 | % Usage: [steps1, steps2] = FindSteps(magdata, phase, in, out); |
| 6 | % |
| 8 | |
| 9 | |
| 10 | |
| 18 | |
| 19 | |
| 20 | CH1 = magdata(:, 1); |
| 21 | CH2 = magdata(:, 2); |
| 22 | |
| 23 | zone1 = (out(1)−100 : out(1))'; |
| 25 | zone2 = (in(1)+100 : in(1)+200)'; |
| 27 | zone3 = (in(2)−200 : in(2)−100)'; |
| 28 | zone4 = (out(2) : out(2)+100)'; |
| 29 | |
| 30 | |
| 31 | p1 = polyfit(zone1, CH2(zone1), 1); |
| 32 | p2 = polyfit(zone2, CH2(zone2), 1); |
| 33 | p3 = polyfit(zone3, CH2(zone3), 1); |
| 34 | p4 = polyfit(zone4, CH2(zone4), 1); |
| 35 | |
| 36 | midpoint1 = round(mean([out(1) in(1)])); |
| 37 | midpoint2 = round(mean([out(2) in(2)])); |
| 38 | |
| 39 | |
| 46 | |
| 47 | |
| 48 | tranest1 = mean([polyval(p2, midpoint1) polyval(p1, midpoint1)]); |
| 49 | |
| 50 | zone = (min(zone1):max(zone2))'; % zone to sarch for the transition |
| 51 | alltrans = magdata(zone,2)>tranest1; |
| 52 | alltrans = abs(diff(alltrans)); |
| 53 | I = abs(find(alltrans)); % Indices of transitions |
| 54 | distances = I + min(zone) − midpoint1; % distances from midpoint (signed) |
| 55 | absdist = abs(distances); |
| 57 | closest = find(absdist == min(absdist)); % The index into distances of the nearest point |
| 58 | closest = closest(1); % in case there are more than 1 |
| 59 | closestdist = distances(closest); % distance of the closest point |
| 60 | closestpos = midpoint1 + closestdist; % Index of closest transition |
| 61 | midpoint1 = closestpos; % Redefine midpoint |
| 62 | |
| 63 | step1 = polyval(p2, midpoint1) − polyval(p1, midpoint1); |
| 64 | |
| 65 | %Now do it again for step 2 |
| 66 | |
| 67 | tranest2 = mean([polyval(p3, midpoint2) polyval(p4, midpoint2)]); |
| 68 | |
| 69 | zone = (min(zone3):max(zone4))'; % zone to sarch for the transition |
| 70 | alltrans = magdata(zone,2)>tranest2; |
| 71 | alltrans = abs(diff(alltrans)); |
| 72 | I = abs(find(alltrans)); % Indices of transitions |
| 73 | distances = I + min(zone) − midpoint2; % distances from midpoint (signed) |
| 74 | absdist = abs(distances); |
| 75 | closest = find(min(absdist)); % The index into distances of the nearest point |
| 76 | closest = closest(1); % in case there are more than 1 |
| 77 | closestdist = distances(closest); % distance of the closest point |
| 78 | closestpos = midpoint2 + closestdist; % Index of closest transition |
| 79 | midpoint2 = closestpos; % Redefine midpoint |
| 80 | |
| 81 | step2 = polyval(p3, midpoint2) − polyval(p4, midpoint2); |
| 82 | |

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

Other embodiments will occur to those skilled in the art and are within the following claims.

What is claimed is:

1. A method of determining the total magnetic content of a fluid sample introduced within at least one coil, the method comprising:
   determining a sample withdrawal event time based on when the fluid sample is withdrawn from within the at least one coil;
   at the sample withdrawal event time, analyzing a measured response signal of the at least one coil in a first time zone before the sample withdrawal event time and determining a first value, and analyzing the measured response signal of the at least one coil in a second time zone after the sample withdrawal event time and determining a second value; and
   calculating a total magnetic content of the fluid sample from the difference between the first value and the second value.

2. The method claim 1 further including:
   determining a sample insertion event time based on when the fluid sample is inserted into the at least one coil;
   at the sample insertion event time, analyzing a measured response signal of the at least one coil in a third time zone before the sample insertion event time and determining a third value, and analyzing the measured response signal of the at least one coil in a fourth time zone after the sample insertion event time and determining a fourth value; and
   determining the total magnetic content of the fluid sample based on weighted values of a) the difference between the first value and the second value and b) the difference between the third value and the fourth value.

3. The method of claim 1 in which analyzing the measured response signal of the at least one coil includes calculating linear regression lines corresponding to the measured response signal in the first and second time zones.

4. The method of claim 3 in which determining the sample withdrawal event time includes employing one or more sensors to detect an initial sample withdrawal event time.

5. The method of claim 4 in which determining the sample withdrawal event time further includes adjusting the initial sample withdrawal event time based on a value half way between the first value and the second value.

6. The method of claim 2 in which analyzing the measured response signal of the at least one coil includes calculating linear regression lines corresponding to the measured response signal in the third and fourth time zones.

7. The method of claim 6 in which determining the sample insertion event time includes employing one or more sensors to detect an initial sample insertion event time.

8. The method of claim 2 in which determining the sample insertion event time further includes adjusting the initial sample insertion event time based on a value half way between the third and fourth values.

9. The method of claim 1 further including one or more additional coils.

10. The method of claim 1 in which analyzing the measured response signal of the at least one coil includes analyzing a real and/or imaginary components of the measured coil response signal.

11. The method of claim 2 in which difference between the first value and the second value is multiplied by a first predetermined factor, and the difference between the third value and the fourth value is multiplied by another predetermined factor which is less than the first predetermined factor.

12. The method of claim 3 in which the first value correspondences to voltage at a best fit straight line corresponding to the linear regression line of the first time zone at the sample withdrawal event time, and the second value corresponds to voltage at a best fit straight line corresponding to the linear regression line of the second time zone at the sample withdrawal event time.

13. The method of claim 6 in which the third value correspondences to voltage at a best fit straight line corresponding to the linear regression line of the third time zone at the sample insertion event time, and the fourth value corresponds to voltage at a best fit straight line corresponding to the linear regression line of the fourth time zone at the sample insertion event time.

* * * * *